US011090380B2

(12) United States Patent
Howard et al.

(10) Patent No.: US 11,090,380 B2
(45) Date of Patent: Aug. 17, 2021

(54) METHODS AND COMPOSITIONS TO INCREASE IMMUNE RESPONSE TO VACCINES

(71) Applicant: Applied Biotechnology Institute, Inc., San Luis Obispo, CA (US)

(72) Inventors: John Howard, San Luis Obispo, CA (US); Celine Hayden, San Louis Obispo, CA (US)

(73) Assignee: Applied Biotechnology Institute, Inc., San Luis Obispo, CA (US)

( * ) Notice: Subject to any disclaimer, the term of this patent is extended or adjusted under 35 U.S.C. 154(b) by 37 days.

(21) Appl. No.: 16/423,839

(22) Filed: May 28, 2019

(65) Prior Publication Data

US 2020/0009246 A1 Jan. 9, 2020

Related U.S. Application Data

(60) Provisional application No. 62/680,412, filed on Jun. 4, 2018.

(51) Int. Cl.
*A61K 39/29* (2006.01)
*A61K 39/39* (2006.01)
*A61K 39/00* (2006.01)

(52) U.S. Cl.
CPC ............ *A61K 39/292* (2013.01); *A61K 39/39* (2013.01); *A61K 2039/517* (2013.01); *A61K 2039/55516* (2013.01); *A61K 2039/55583* (2013.01)

(58) Field of Classification Search
CPC .......... A61P 37/04; A61P 15/08; A61P 31/20; A61P 43/00; A61K 2039/53; A61K 2039/55511; A61K 2039/5256; A61K 9/127; A61K 9/1652; A61K 9/1658; A61K 39/002; A61K 39/29; A61K 39/012; A61K 39/12; A61K 39/292; A61K 39/005; C12N 15/86; C12Y 207/07; B01F 13/0094; C07K 14/415
See application file for complete search history.

(56) References Cited

U.S. PATENT DOCUMENTS

| | | | |
|---|---|---|---|
| 5,484,719 | A | 1/1996 | Lam et al. |
| 5,612,487 | A | 3/1997 | Lam et al. |
| 5,767,379 | A | 6/1998 | Baszczynski et al. |
| 5,824,870 | A | 10/1998 | Baszczynski et al. |
| 5,914,123 | A | 6/1999 | Arntzen et al. |
| 6,034,298 | A | 3/2000 | Lam et al. |
| 6,087,558 | A | 7/2000 | Howard et al. |
| 6,136,320 | A | 10/2000 | Arntzen et al. |
| 6,504,085 | B1 | 1/2003 | Howard |
| 7,183,109 | B2 | 2/2007 | Streatfield et al. |
| 9,492,547 | B2 | 11/2016 | Cooper et al. |
| 2014/0205625 | A1 | 7/2014 | Howard et al. |

OTHER PUBLICATIONS

Arakawa et al., "Stabilization of Protein Structure by Sugars", Biochemistry, vol. 21, pp. 6536-6544, 1982.
Bailey, Michele Renee, "A Model System for Edible Vaccination Using Recombinant Avidin Produced in Corn Seed", A Thesis for Graduate Studies at Texas A&M University, 90 pages, Dec. 2000.
Boisen, S., "Protease Inhibitors in Cereals", Acta Agriculture Scandinavica, vol. 33:4, pp. 369-381, 1983.
Brandtzaeg et al., "Mucosal B cells: phenotypic characteristics, transcriptional regulation, and homing properties", Immunological Reviews, vol. 206, pp. 32-63, 2005.
Cuburu et al., "Sublingual immunization induces broad-based systemic and mucosal immune responses in mice", Vaccine, vol. 25, pp. 8598-8610, Sep. 25, 2007.
Czerkinsky et al., "Mucosal delivery routes for optimal immunization: Targeting immunity to the right tissues", Current Topics in Microbiology and Immunology, vol. 354, pp. 1-18, 2012.
Egelkrout et al., "Enhanced Expression Levels of Cellulase Enzymes Using Multiple Transcription Units", Bioenerg. Res., vol. 6, pp. 699-710, 2013.
Fischer et al., "Plant-based production of biopharmaceuticals", Current Opinion in Plant Biology, vol. 7, pp. 152-158, 2004.
Hayden et al., "Oral delivery of wafers made from HBsAg-expressing maize germ induces long-term immunological systemic and mucosal responses", Vaccine, vol. 33(25), pp. 2881-2886, Jun. 9, 2015.
Hayden et al., "Production of highly concentrated, heat stable hepatitis B surface antigen in maize", Plant Biotechnology Journal, vol. 10, pp. 979-984, May 30, 2012.
Hayden et al., "Supercritical fluid extraction provides an enhancement to the immune response for orally-delivered hepatitis B surface antigen", Vaccine, vol. 32, pp. 1240-1246, Jan. 14, 2014.
Honda-Okubo et al., "Advax™, a polysaccharide adjuvant derived from delta inulin, provides improved influenza vaccine protection through broad-based enhancement of adaptive immune responses", Vaccine, vol. 30(36), pp. 5373-5381, Aug. 3, 2012.
Hood et al., "Commercial production of avidin from transgenic maize; characterization of transformant, production, processing, extraction and purification", Molecular Breeding, vol. 3, pp. 291-306, Apr. 7, 1997.
Hood et al., "Manipulating corn germplasm to increase recombinant protein accumulation", Plant Biotechnology Journal, vol. 10, pp. 20-30, 2012.

(Continued)

*Primary Examiner* — Bao Q Li
(74) *Attorney, Agent, or Firm* — McKee, Voorhees & Sease, PLC

(57) ABSTRACT

Methods of vaccination of animals are provided. In an embodiment, a paired administration of a primer vaccine provides for non-oral administration of a vaccine and an oral administration of the vaccine and can be followed by a paired administration of a booster vaccine of a non-oral administration and an oral administration. Embodiments provide the non-oral and oral administration are within three days of each other. The methods provide for improved protective response in an animal compared to administration of a primer non-oral administered vaccine followed by three booster non-oral administered vaccines. An adjuvant is provided that is a microcrystalline polysaccharide-based adjuvant derived from delta inulin.

19 Claims, 12 Drawing Sheets

(56) References Cited

OTHER PUBLICATIONS

Hood et al., “Criteria for high-level expression of a fungal laccase gene in transgenic maize”, Plant Biotechnology Journal, vol. 1, pp. 129-140, 2003.
Huang et al., “High-yield rapid production of hepatitis B surface antigen in plant leaf by a viral expression system”, Plant Biotechnology Journal, vol. 6, pp. 202-209, 2008.
Kapusta et al., “A plant-derived edible vaccine against hepatitis B virus”, The FASEB Journal, vol. 13, pp. 1796-1799, Oct. 1999.
Kong et al., “Oral immunization with hepatitis B surface antigen expressed in transgenic plants”, PNAS, vol. 98, No. 20, pp. 11539-11544, Sep. 25, 2001.
Kumar et al., “Production of Hepatitis B Surface Antigen in Recombinant Plant Systems: An Update”, Biotechnol. Prog., vol. 23, pp. 532-539, 2007.
Lamphear et al., “Delivery of subunit vaccines in maize seed”, Journal of Controlled Release, vol. 85, pp. 169-180, Mar. 4, 2002.
Lappalainen et al., “Protection against live rotavirus challenge in mice induced by parenteral and mucosal delivery of VP6 subunit rotavirus vaccine”, Arch Virol., vol. 160, pp. 2075-2078, May 29, 2015.
Mason et al., “Expression of Norwalk virus capsid protein in transgenic tobacco and potato and its oral immunogenicity in mice”, Proc. Natl. Acad. Sci., vol. 93, pp. 5335-5340, May 1996.
Mason et al., “Edible vaccine protects mice against *Escherichia coli* heat-labile enterotoxin (LT): potatoes expressing a synthetic LT-B gene”, Vaccine, vol. 16, No. 13, pp. 1336-1343, 1998.
McCluskie et al., “Parenteral and mucosal prime-boost immunization strategies in mice with hepatitis B surface antigen and CpG DNA”, FEMS Immunology and Medical Microbiology, vol. 32, pp. 179-185, 2002.
Petrovsky et al., “Advax™, a novel microcrystalline polysaccharide particle engineered from delta inulin, provides robust adjuvant potency together with tolerability and safety”, Vaccine, vol. 33(44), pp. 5920-5926, Nov. 4, 2015.
“Polio vaccine most effective when oral, injectable doses used in tandem, study finds”, National Post, https://nationalpost.com/health/polio-vaccine-most-effective-when-oral-injectable-doses-used-in-tandem-study-finds, 5 pages, accessed Dec. 11, 2017.
Song et al., “Sublingual vaccination with influenza virus protects mice against lethal viral infection”, PNAS, vol. 105, No. 5, pp. 1644-1649, Feb. 5, 2008.
Streatfield et al., “Corn as a production system for human and animal vaccines”, Vaccine, vol. 21, pp. 812-815, 2003.
Streatfield et al., “Plant based vaccines: unique advantages”, Vaccine, vol. 19, pp. 2742-2748, 2001.
Streatfield et al., “Development of an edible subunit vaccine in corn against Enterotoxigenic strains of *Escherichia coli*”, In Vitro Cell. Dev. Bio.—Plant, vol. 38, pp. 11-17, Jan. 2002.
Tacket et al., “Immunogenicity of recombinant LT-B delivered orally to humans in transgenic corn”, Vaccine, vol. 22, pp. 4385-4389, Jan. 6, 2004.
Thanavala et al., “Immunogenicity of transgenic plant-derived hepatitis B surface antigen”, Proc. Natl. Acad. Sci., vol. 92, pp. 3358-3361, Apr. 1995.
Thanavala et al., “Immunogenicity in humans of an edible vaccine for hepatitis B”, PNAS, vol. 102, No. 9, pp. 3378-3382, Mar. 1, 2005.
Van Damme et al., “Persistence of antibodies 20 y after vaccination with a combined hepatitis A and B vaccine”, Human Vaccines & Immunotherapeutics, vol. 13, No. 5, pp. 972-980, 2017.
Wigdorovitz et al., “Protection of Mice against Challenge with Foot and Mouth Disease Virus (FMDV) by Immunization with Foliar Extracts from Plants Infected with Recombinant Tobacco Mosiac Virus Expressing the FMDV Structural Protein VP1”, Virology, vol. 264, pp. 85-91, Jul. 23, 1999.
Witcher et al., “Commercial production of p-glucuronidase (GUS): a model system for the production of proteins in plants”, Molecular Breeding, vol. 4, pp. 301-312, Jan. 29, 1998.
Wong, Sam, “Injected vaccine could help eradicate polio”, Imperial College London, http:// www3.imperial.ac.uk/newsandeventspggrp/imperialcollege/news, 3 pages, Jul. 11, 2014.
Woodard et al., “Maize-derived bovine trypsin: Characterization of the first large-scale, commercial protein product from transgenic plants”, Biotechnol. & Appl. Biochem., 25 pages, May 15, 2003.
Wu et al., “Immunization of Chickens with VP2 Protein of Infectious Bursal Disease Virus Expressed in Arabidopsis thaliana”, Avian Diseases, vol. 48, No. 3, pp. 663-668, Sep. 2004.
Zhong et al., “Commercial production of aprotinin in transgenic maize seeds”, Molecular Breeding, vol. 5, pp. 345-356, 1999.

METHODS AND COMPOSITIONS TO INCREASE IMMUNE RESPONSE TO VACCINES

CROSS-REFERENCE TO RELATED APPLICATIONS

This application claims priority under 35 U.S.C. § 119 to provisional application Ser. No. 62/680,412, filed Jun. 4, 2018 which is herein incorporated by reference in its entirety.

STATEMENT REGARDING FEDERALLY SPONSORED RESEARCH

This invention was made with Government support under contract (Contract No. HHSN272201600035C), NIH MARC T34-GM008574 (JEG) awarded by National Institute of Allergy and Infectious Diseases, part of the National Institutes of Health. The Government has certain rights in this invention.

BACKGROUND

Current vaccination protocols typically require administration of a priming parental vaccination and subsequent boosting parental vaccinations. These vaccinations commonly produce a serum response in the subject. One problem with such regimes is they produce only serum response and the multiple subsequent vaccinations cause issues with compliance with the regime and access to multiple vaccination protocols where administered to subjects in remote areas.

By way of example, an estimated two billion people have been infected with the hepatitis B virus (HBV) worldwide, with approximately 240 million suffering chronic symptoms [1]. The prevalence of HBV exposure and chronic illness is shocking considering there is a vaccine on the market that induces seroconversion of over 85% of those undergoing the 3-injection dose regime [2]. In the U.S., there are one million individuals who suffer from chronic HBV infection [3], and 15-25% go on to develop cirrhosis of the liver and liver cancer [4].

Some populations, such as celiac disease patients, inflammatory bowel disease patients, chronic kidney disease patients, obese individuals, the elderly, and immunocompromised individuals are at increased risk of a poor antibody response to the parenteral 3-dose regime [5-10]. Additionally, incomplete vaccination regimes contribute to populations at increased risk of developing chronic infections. Specifically, completion of the hepatitis B second and third boosting dose is low among healthcare workers [11-13], yet they have increased exposure to HBV as a result of their profession. Most healthcare workers are well aware that HBV is ten times more infectious than HIV and one million Americans harbor the virus as a chronic hepatitis B infection, so there are clearly other factors which influence healthcare workers' avoidance of second and third injections.

The currently commercialized vaccine, the hepatitis B surface antigen (HBsAg), is a subunit vaccine that is parenterally administered in three doses over 6 to 12 months. A more efficacious vaccine for non-responding populations and a dosing regimen shortened to two dosing days or two paired administrations when the paired administrations are within three days from one another. This would clearly improve vaccine coverage in the population as a whole for vaccination against a disease or microorganism, such as hepatitis B. Alternatives to parenteral HBsAg administration, such as intradermal delivery, have shown significantly higher seroconversion rates in non-responding populations [14-16]. In addition, vaccine research for other diseases has demonstrated that a combination of intramuscular and mucosal delivery is more protective than either one alone [17, 18].

BRIEF SUMMARY

Provided here are methods of increase a protective response to a vaccine and where the protective response is achieved by giving a paired vaccination, one oral and one non-oral within three days of the other. This can also be used as booster with two vaccinations, one primer vaccination and a second booster vaccination. An embodiment of the invention provides for a first paired administration of the vaccine comprising an oral administration and a non-oral administration, administered within three days from one another and a booster vaccination of a second paired administration also comprising an oral administration and a non-oral administration, administered within three days from one another. In an embodiment the paired administrations may be administered on the same day. Further embodiments provide the first paired administration and the second paired administration are administered within two weeks of the other. The oral administration in certain embodiments is administration of plant material comprising a nucleic acid molecule "subunit" which may encode amino acids of the pathogen. Embodiments provide for an increased protective response compared to a protocol of three parental administrations, administering a priming parental administration and two booster parental administrations. Additional embodiments provide for a serum and mucosal immune response. Yet further embodiments provide for the vaccine to comprise a microcrystalline poly saccharide-based adjuvant derived from delta inulin.

DESCRIPTION

Figure 1:
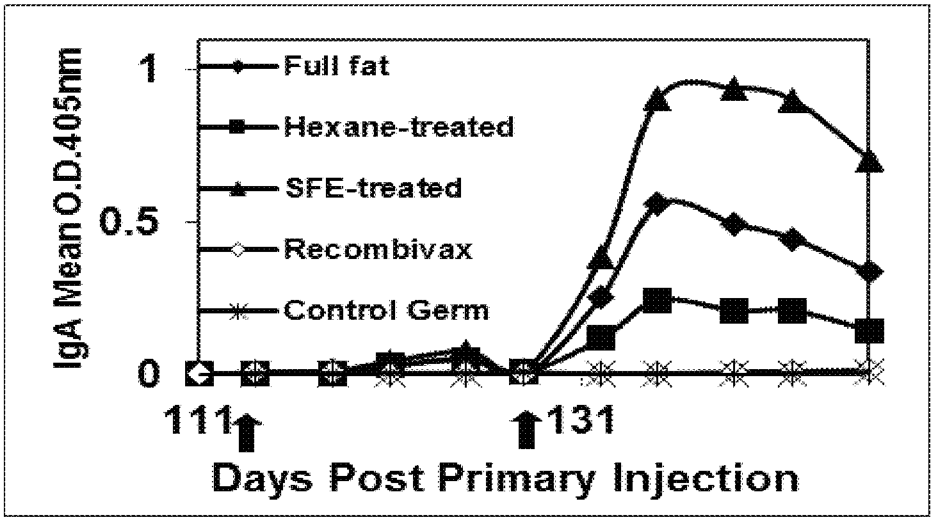
FIG. 1 is a graph showing fecal IgA response in mice with full-fat or defatted material. Mice were boosted (black arrows) orally with maize-produced HBsAg, parenterally with the commercial vaccine (Recombivax®), or fed control germ as a negative control. Only the orally delivered maize-produced HBsAg material resulted in an increase in mucosal titers. Furthermore, the SFE treatment material showed the strongest immunogenic response compared to either hexane treatment or full-fat material.

The following outlines improvements to vaccination of animals. In one embodiment, the vaccine composition may include an adjuvant which is a microcrystalline polysaccharide-based adjuvant derived from delta inulin, such as Advax™. In another embodiment, the protective response of the vaccine may be increased by administering both an oral dose of the vaccine and a non-oral dose of the vaccine. Thus, when vaccinating the animal, both types of vaccine are administered to the animal. An embodiment of the invention provides for a first paired administration of the vaccine comprising an oral administration and a non-oral administration, administered within three days from one another and a booster vaccination of a second paired administration also comprising an oral administration and a non-oral administration, administered within three days from one another.

In one embodiment, a nucleic acid molecule is introduced into a plasmid or vector or expression cassette that in turns produces a protein that can be administered to the animal. An example provided here is of producing a vector comprising a hepatitis B surface antigen, a so-called subunit vaccine. Another embodiment provides the nucleic acid molecule can be introduced into a plant, by transformation of plant cells or via plant breeding techniques from a plant so transformed, and from which an oral vaccine may be prepared. An example of production of a plant expressing the hepatitis B surface antigen is found at US Patent Publication No. US 20140205625, the contents of which are incorporated herein by reference in its entirety. Transgenic plants can be successfully used to express a variety of useful proteins. For example, production of proteases in plants has been achieved (See U.S. Pat. No. 6,087,558); along with production of aprotinin in plants (U.S. Pat. No. 5,824,870); and avidin (U.S. Pat. No. 5,767,379). A variety of mammalian bacterial and viral pathogen antigens are included in those proteins that have been successfully produced in plants, such as viral vaccines (U.S. Pat. No. 6,136,320), transmissible gastroenteritis and hepatitis vaccines (U.S. Pat. Nos. 5,914,123 and 6,034,298). These patents, as well as all references cited herein are incorporated herein by reference. Such peptides can induce an immunogenic response in mice (Mason et al. (1998) Vaccine 16:13361343; Wigdorovitz et al. (1999) Virology 155:347-353), and humans (Kapusta et al. (1999) FASEB J. 13:1796-1799). After oral delivery, these vaccine candidates were immunogenic and could induce protection. Mice fed a basic diet plus corn expressing recombinant *Escherichia coli* heat-labile enterotoxin B-subunit (LtB) mounted a dose dependent IgG and IgA response (Streatfield et al. (2001) "Plant based vaccines—unique advances" Vaccine 19:2742-2748.) Some of the first edible vaccine technologies developed include transgenic potatoes expressing hepatitis B, TGEV and Norwalk virus antigens as well as various other viral antigens. (See, e.g., Thanavala et al. (1995) Proc. Natl. Acad. Sci. U.S.A. 92:3358-3361; U.S. Pat. Nos. 6,136,320; 6,034,298; 5,914,123; 5,612,487 and 5,484,719; Mason et al., (1996) Proc. Natl. Acad. Sci. 93:5335-5340;"VP1 protein for foot-and-mouth disease" (Wigdorovitz et al (1999) Virology 255:347-353).

The methods can be applied to any microorganism/pathogen that causes adverse impact in an animal and is not limited to any particular such microorganism or animal. In particular, the present invention provides for methods to immunize against, or to prevent or to reduce the symptoms caused by, infection of such an animal with a pathogenic organism. Thus, when referring to a microorganism it is meant to include any such disease-causing agent, for example, a virus, bacteria, fungus, or protozoan parasite. Protection from disease is provided by the vaccine of the invention, that is, protection from all or some of the adverse impact on the animal's health.

In particular, the present processes provide for methods to immunize against, or to prevent or to reduce the symptoms caused by, infection of an animal with a pathogenic organism (for example, infection by a virus, bacteria, fungus, or protozoan parasite). The method of the present invention is useful in vertebrate animals including, but not limited to, humans, canine (e.g., dogs), feline (e.g., cats); equine (e.g., horses), bovine (e.g., cattle), ovine (e.g. sheep), caprine (e.g. goat) porcine animals (e.g., pigs) and rabbit, as well as in avians including, but not limited to, chickens, turkeys, ducks, geese, a quail, a pheasant, parrots, finches, hawks, crows and ratites (ostrich, emu, cassowary, and the like) as well as domestic fur animals such as ferrets, minks, mustilids, and fish such as fin-fish, shellfish, and other aquatic animals. Fin-fish include all vertebrate fish, which may be bony or cartilaginous fish. Any fish species susceptible to disease may benefit. The methods may also be used with invertebrates, including aquatic invertebrates.

As used herein, the term "vaccine" as used herein refers to a pharmaceutical composition comprising at least one protective molecule, that induces protective response in an animal and possibly, but not necessarily, one or more additional components that enhance the activity of said active component. Embodiments provide for a nucleic acid molecule encoding an amino acid of the microorganism. A vaccine may additionally comprise further components typical to pharmaceutical compositions. In another form, the immunologically active component of a vaccine may comprise appropriate elements of said organisms (subunit vaccines) whereby these elements are generated either by destroying the whole organism or the growth cultures of such microorganisms and subsequent purification steps yielding in the desired structure(s), or by synthetic processes induced by an appropriate manipulation of a suitable system such as, but not restricted to, bacteria, insects, mammalian, or other species, plus subsequent isolation and purification procedures or by induction of said synthetic processes in the animal needing a vaccine by direct incorporation of genetic material using suitable pharmaceutical compositions (polynucleotide vaccination). A vaccine may comprise one or simultaneously more than one of the elements described above.

The terms "protecting", "protection", "protective immunity" or "protective immune response," as used herein, are intended to mean that the host animal mounts an active immune response to the vaccine or polynucleotides or polypeptides described here, such that upon exposure to disease challenge, the animal is able to combat the infection. Thus, a protective immune response will decrease the incidence of morbidity and mortality from exposure to the microorganism among a host animal. The animal will be protected from subsequent exposure to the disease-causing agent. In an embodiment, the animal may be protected by treating the animal which has already been exposed to the disease-causing agent by administration of the vaccine after such exposure. In such an instance there is also shown to be a lessening of morbidity and mortality. Those skilled in the art will understand that in a commercial animal setting, the production of a protective immune response may be assessed by evaluating the effects of vaccination on the herd as a whole, e.g., there may still be morbidity and mortality in a minority of vaccinated animals. Furthermore, protection also includes a lessening in severity of any gross or histopathological changes and/or of symptoms of the disease, as compared to those changes or symptoms typically caused by the isolate in similar animals which are unprotected (i.e., relative to an appropriate control). Thus, a protective immune response will decrease the symptoms of the disease, which will vary according to the disease. In certain instances, the animal may not necessarily produce antibodies that can be measured, yet disease morbidity and/or mortality is reduced and where there also may be a reduced titer of infection upon exposure to the microorganism. In other instances, there may be a production of antibodies. The amount of IgM, IgA, IgG or other antibodies may increase. In other instances, the amount of T-cells may be increased, lymphocytes produced in the thymus and having a T-cell receptor, or B cells, which mature in bone marrow and have B-cell receptors.

In one embodiment the administration of the vaccine results in decreased weight loss after exposure to the pathogen. By way of example without limitation, the animal weight loss is reduced such that the animal receiving the vaccine has up to 6%, 6.5%, 7%, 7.5%,8%, 8.5%, 9%, 9.5% 10% or more, or amounts in-between greater weight than an animal not receiving the vaccine.

As used herein, "immunogenically effective amount" refers to an amount, which is effective in reducing, eliminating, treating, preventing or controlling the symptoms of the infections, diseases, disorders, or condition.

Vaccines are "administered" in an embodiment of the methods by oral delivery, and also by non-oral delivery. Non-oral delivery may be, for example, parenteral, injection subcutaneously or intramuscularly, into an organ or cavity of the animal; may be by transdermal or by gas exchange. The vaccine can be administered by non-oral means which includes, but is not limited to, syringes, nebulizers, misters, needleless injection devices, or microprojectile bombardment gene guns (Biolistic bombardment), via a liposome delivery system, naked delivery system, electroporation, viruses, vectors, viral vectors. The immunogenic preparations and vaccines are administered in a manner compatible with the dosage formulation, and in such amount as will be therapeutically effective, immunogenic and protective.

The quantity to be administered depends on the subject to be treated, including, for example, the capacity of the immune system of the individual to mount a protective response. In an embodiment the present methods provide for an initial dose of both oral and non-oral administration of the vaccine. Another embodiment provides for a second such administration of both oral and non-oral delivery. The result is a protective response which includes an increased immune response compared to either parental alone or oral alone and reduces the number of administrations of the vaccine necessary. The present method can be included with other boosting regimes if desired.

In one example, the animal receives two doses, that is, one delivery of the vaccine that provides a protective response to one or more diseases via non-oral such as injection and also receives a second and commonly a third (or more) delivery of the vaccine providing protective response to those same diseases via oral delivery. The first dose is referred to as a priming dose, as this is administered to activate/alert immune cells to presence of the microorganism. It primes memory cells and typically produces IgM antibodies which later are not seen. IgM producing plasma cells migrate from the lymph node to bone marrow during the initial response to an antigen or microbe. It can bind to antigens without prior immunization. In general, it is often produced one week after exposure. This first vaccination is often referred to as a "prime" vaccination or "primer" since it in essence alerts the immune system. Vaccination protocols then utilizer "booster" vaccinations subsequent to the first vaccination. This then produces further antibodies. This includes Immunoglobulin A (IgA) found in high concentration sin the mucosal tissue; Immunoglobulin G (IgG) found in all body fluids including blood; Immunoglobulin E (IgE) found in lungs, skin and mucous membranes; and Immunoglobulin D (IgD) found in the blood. For example, a common protocol for vaccination of hepatitis B is a prime vaccination followed by two booster doses. (See, e.g., Van Damme et al. (2017) "persistence of antibodies 20 y after vaccination with a combined hepatitis A and B vaccine" hum. Vaccin. Immunother. 13(5):972-980 where boosters were administered one and six months after the prime vaccination.)

In the present methods, there is provided a paired administration of the primer vaccine followed by a paired second administration of a booster vaccination. An embodiment provides the paired vaccination comprises an oral administration of the vaccine and an injected administration of the vaccine. The oral and injected administration occurs at the same time up to and include three days after the other form is administered. In other words, the oral administration occurs, followed by non-oral administration; or the non-oral administration occurs followed by oral administration; or both are administered at the same time. When not administered together, it does not matter if the oral administration is delivered first or second. This primer paired vaccination acts to activate the immune system.

Following this first administration of the paired vaccines, a second paired administration of the booster vaccine occurs. Again, an embodiment provides the oral and injected administration occurs at the same time up to and including three days after the other form is administered.

In an embodiment the vaccines, both non-oral and oral, provide the same subunit vaccine, adjusted for dosage via non-oral versus oral delivery.

Embodiments of the methods can provide for multiple booster administrations. For example, the subject may receive two, three, four, five, six seven, eight, nine, ten or more booster administrations. The third or more booster administrations may be paired or not paired administrations and may be oral, parental or other delivery. Surprisingly, however, it has been found that this administration of the vaccine of a first paired administration and a second paired administration produces an increased protective response compared to three parental administration of the vaccine, provided as a first primer and two booster parental administrations. When administered by the methods described here, the primer and booster paired administrations produced an increased immune response, and in embodiments produced increase IgG and/or IgA response compared to three parental administrations. Further embodiments provide for an increased protective response utilizing the primer and booster paired administration. In addition to providing an improved protective and/or immune response, including a synergistic response, the methods here allow for a reduced number of vaccinations. This is particularly useful in obtaining compliance for vaccination protocols and when vaccinating in locations where reaching the person or animal in need of vaccination is difficult. Further, this reduces cost in administration of vaccines.

The timing between the first paired administration of the primer vaccination and the second paired administration of the booster vaccine will vary depending upon the microorganism and the subject involved. For example, in humans vaccinated with hepatitis B vaccine, one example is administration within one to six months after the primer vaccination. In another example, poultry and fish may receive a booster vaccination within about three weeks after a primer vaccination. Booster vaccination for mice is often three weeks after the primer vaccination. However, the time will vary. By way of example without limitation, the booster may be administered in about two weeks after the primer vaccination but could also be months or even years later. Some boosters are provided yearly. One of skill in the art will appreciate that the timing of the booster vaccination will be determined by the microorganism and subject characteristics. By way of example, one can determine when the immune response is increasing and when it begins to decrease after the primer vaccination. By way of example, antibodies specific to the disease/microorganism can be detected from a sample from a representative subject. By further example presents of B and T cell activity after primer administration may be tracked. When the immune response has achieved peak and/or is beginning to decrease, may be a preferred time to administer the booster vaccination.

In further embodiments, the polysaccharide adjuvant derived from delta inulin, Advax™ is administered with the vaccine. Inulin is a polysaccharide obtained from plants that when in the delta polymorphic form is immunologically active. See Honda-Okubo et al. (2012) "Advax™, a polysaccharide adjuvant derived from delta inulin, provides improved influenza vaccine protection through broad-based enhancement of adaptive immune responses" Vaccine 30(36):5373-5381; Cooper et al. U.S. Pat. No. 9,492,547, incorporated herein by reference in its' entirety.

The method of the present invention is useful in any animal, such as vertebrate animals including, but not limited to, humans, canine (e.g., dogs), feline (e.g., cats); equine (e.g., horses), bovine (e.g., cattle), ovine (e.g. sheep), caprine (e.g. goat) porcine animals (e.g., pigs) and fish such as fin-fish, shellfish, and other aquatic animals. A few examples, without intending to be limiting, of diseases with which the methods may be used include hepatitis B virus, Cholera, tetanus toxoid, diphtheria toxoid, Human immunodeficiency virus, Orthoreovirus, Rotavirus, Ebolavirus, influenza, Measles virus, Mumps virus, Rubella virus, Pneumovirus, Human respiratory syncytial virus, Rabies virus, California encephalitis virus, Japanese encephalitis virus, Hantaan virus, Lymphocytic choriomeningitis virus, Coronavirus, Enterovirus, Rhinovirus, Poliovirus, Norovirus, Flavivirus, Dengue virus, West Nile virus, Yellow fever virus and *varicella, Anthrax, Brucella, Candida, Chlamydia pneumoniae, Chlamydia psittaci, Cholera, Clostridium botulinum, Coccidioides immitis, Cryptococcus, Diphtheria, Escherichia coli* 0157: H7, *Enterohemorrhagic Escherichia coli, Enterotoxigenic Escherichia coli, Haemophilus influenzae, Helicobacter pylori, Legionella, Leptospira, Listeria, Meningococcus, Mycoplasma pneumoniae, Mycobacterium, Pertussis, Pneumonia, Salmonella, Shigella, Staphylococcus, Streptococcus pneumoniae*, Bovine Viral Diarrhea, *Clostridium difficile*, and Foot and Mouth Disease virus (FMDV).

The term plant or plant material or plant part is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. The tissue culture will preferably be capable of regenerating plants. Preferably, the regenerable cells in such tissue cultures will be embryos, protoplasts, meristematic cells, callus, pollen, leaves, anthers, roots, root tips, silk, flowers, kernels, ears, cobs, husks or stalks. Still further, provided are plants regenerated from the tissue cultures.

As used herein, the terms nucleic acid or polynucleotide refer to deoxyribonucleotides or ribonucleotides and polymers thereof in either single- or double-stranded form. The protective sequence used to make the vaccine may an isolated sequence or synthetically produced. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene.

Nucleic acids include those that encode an entire polypeptide or produce an RNA sequence as well as those that encode a subsequence of the polypeptide or RNA or produce a fragment of an interfering RNA. For example, the process includes nucleic acids that encode a polypeptide or RNA which is not full-length but nonetheless has protective activity. The methods include not only nucleic acids that include the nucleotide sequences as set forth herein, but also nucleic acids that are substantially identical to, correspond to, or substantially complementary to, the exemplified embodiments. For example, the processes includes nucleic acids that include a nucleotide sequence that is at least about 70% identical to one that is set forth herein, more preferably at least 75%, still more preferably at least 80%, more preferably at least 85%, 86%, 87%, 88%, 89% still more preferably at least 90%, 91%, 92%, 93%, 94%, and even more preferably at least about 95%, 96%, 97%, 98%, 99%, 100% identical (or any percentage in between) to an exemplified nucleotide sequence. The nucleotide sequence may be modified as described previously, so long as any polypeptide encoded or RNA or dsRNA produced is capable of inducing the generation of a protective response.

As used herein, a "polypeptide" refers generally to peptides and proteins. In certain embodiments the polypeptide may be at least two, three, four, five, six, seven, eight, nine or ten or more amino acids or more or any amount in-between. The terms "fragment," "derivative" and "homologue" when referring to the polypeptides means a polypeptide which retains essentially the same biological function or activity as said polypeptide, that is, act as an antigen and/or provide treatment for and/or protection against disease. Such fragments, derivatives and homologues can be chosen based on the ability to retain one or more of the biological activities of the polypeptide, that is, act as an antigen and/or provide treatment for and/or protection against the pathogen. The vaccines in an embodiment may be recombinant polypeptides, natural polypeptides or synthetic polypeptides, preferably recombinant polypeptides A "vector" is any means for the transfer of a nucleic acid into a host cell. A vector may be a replicon to which another DNA segment may be attached so as to bring about the replication of the attached segment. The term "vector" includes both viral and nonviral means for introducing the nucleic acid into a cell in vitro, ex vivo or in vivo. Viral vectors include alphavirus, retrovirus, adeno-associated virus, pox, baculovirus, vaccinia, herpes simplex, Epstein-Barr, rabies virus, vesicular stomatitis virus, and adenovirus vectors. Non-viral vectors include, but are not limited to plasmids, liposomes, electrically charged lipids (cytofectins), DNA- or RNA protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

A "cassette" refers to a segment of DNA that can be inserted into a vector at specific restriction sites. The segment of DNA encodes a polypeptide of interest or produces RNA, and the cassette and restriction sites are designed to ensure insertion of the cassette in the proper reading frame for transcription and translation.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode a protective polypeptide are preferably optimized for expression in a particular host cell (e.g., yeast, mammalian, plant, fungal, and the like) used to produce the polypeptide or RNA.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., "Basic Methods in Molecular Biology" Appleton & Lange, Norwalk, Conn. (1994). Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, 1984, Proteins).

Examples are provided by way of exemplification and are not intended to limit the scope of the invention. All references cited herein are incorporated herein by reference.

EXAMPLES

Example 1

We have developed a HBsAg vaccine candidate that is delivered orally in a wafer formulation. Our oral vaccine elicits strong mucosal antibody titers and a significant systemic response while the commercial vaccine shows no evidence of mucosal antibody production in mice but a strong systemic response [19, 20]. Immune responses arising from combined oral and parenteral modes of delivery, therefore, could clearly complement one another. Our oral vaccine candidate may activate sublingual antigen presenting cells (APCs) in the mouth [21, 22] as well as APCs in Peyer's Patches of the gut [23], two sites which can, combined, induce mucosal antibodies at all major mucosa in the body, including the reproductive tract, the respiratory tract, and the gastrointestinal tract [24]. HBV infection is most commonly transmitted i) sexually and ii) during percutaneous exposure to blood [25]; therefore, an injected/oral paired vaccine could bolster the immune response at primary sites of hepatitis B infection (systemically and mucosally), and may help improve antibody titers in non-responders.

This work regards developing a more efficacious vaccine that demonstrates improved antibody responses both systemically and mucosally and decrease the required number of dosing days relative to the 3-dose parenteral vaccine. This proposal contributes to the goal of developing a more efficacious HBV vaccine and provides a unique opportunity to advance a highly prized next generation vaccine towards commercialization, by pairing an existing parenteral commercial product with a safe and effective oral vaccine platform. At the present time, there are still large portions of the population that do not get immunized worldwide or who need repeated boosters due to weak immunological responses, and an improved HBV vaccine would have a major impact in controlling the disease. This product has a high probability of commercialization and should enjoy rapid adoption for the following reasons:

1. Interest and enthusiasm for this product from pharmaceutical company representatives
2. Cost of raw materials for an oral vaccine is projected to be extremely low (<$0.01 per dose)
3. Delivery of oral vaccines is convenient
4. Proven efficacy of the oral vaccine in terms of mucosal responses, systemic responses and long-term immunologic memory in a mouse model [19, 20, 26]
5. Individuals treated with a 2-dose paired injected/oral vaccine still receive the immunological benefit of the injected vaccine. Therefore, no increased risk is associated with testing the candidate vaccine in human clinical trials, only the benefit of improving their mucosal or systemic protection with the oral component.

Because of the advantages of using a plant-produced vaccine and the importance of HBV, many research groups have attempted to develop an oral vaccine against HBV

[27-35]. Expression of HBsAg, the antigen used in commercial parenteral vaccines, has been achieved in potato and, when orally delivered as a booster, has elicited antibody titers in mice [30] and humans [36]. Potato HBsAg induced seroprotection in 58% of volunteers in the clinical trial, providing proof of principle. However, several technical hurdles could not be overcome. Individuals were required to eat 100 g of raw potato which is an impractical dose volume and is not easily consumed due to indigestible starch. Higher levels of antigen could reduce the dose but have not been achieved in potato to date. In addition, potato tissue must be boiled to produce a digestible product, a process which heat-inactivates the antigen [30]. These hurdles must be overcome before potato can become a commercially viable option for oral vaccination. Higher HBsAg levels have been achieved in tobacco leaves [37], but this platform is not edible and requires purification of the protein to remove toxins and proteases. Unfortunately, purified proteins rapidly degrade in the digestive tract and therefore are poor candidates for oral delivery [38]. Purification also adds a significant cost factor which offsets the advantage of using plant material. Other plant-produced hosts have also been attempted but none have combined commercial feasibility and vaccine efficacy to produce a viable candidate.

Our group has overcome these limitations by developing innovations in the maize expression system that produce oral vaccines with robust immunological responses and have demonstrated commercial potential. The significant advantages of expressing HBsAg in maize for vaccine production are briefly discussed below, followed by the technological improvements that we have developed to establish maize as a practical oral delivery platform.

Advantages of Using Maize Grain

High protein expression. Molecular biology techniques combined with breeding strategies, whereby transgenes can be introgressed into variant germplasm to boost expression, have produced some of the highest levels of foreign protein accumulation in plants [39-41].

Production of highly immunogenic material. A key aspect of this system is that the antigen must survive the digestive tract long enough to elicit an immune response in animals. Maize grain can protect recombinant protein against degradation in the digestive tract whereas equal amounts of purified protein are completely degraded when given orally to animals [38]. This is referred to as bioencapsulation and is most likely due to protease inhibitors naturally present in the grain and carbohydrates available for stabilization of the protein, conditions that naturally help protect proteins during seed dormancy [42, 43].

Several maize-based vaccine candidates have provided protective responses upon oral administration and challenge with pathogens in mice, pigs, chicken, sheep, and fish [44-48]. For example, when we orally administered a maize-produced vaccine candidate, TGEV-S, to pigs and challenged them with transmissible gastroenteritis virus (TGEV), complete protection was observed [46]. We also demonstrated that maize-produced LTB provided protection in small animals to the heat labile toxin from *E. coli* and elicited antibodies in humans without any adverse health effects [46, 49-51]. These pathogen challenge experiments further demonstrate that highly immunogenic glycosylated proteins are produced in plants and provide protection in animal models.

Formulation and storage. Whole grain or processed material containing recombinant proteins can be stable at ambient temperatures for years [46, 49, 52]. Maize grain can be easily processed and blended to give a precise antigen dose [46, 49, 50] and can be made palatable and stable without the need for refrigeration during storage and distribution, eliminating the cold chain.

Product safety. Maize grain is inherently safe since the grain does not harbor human or animal pathogens. Maize has "Generally Recognized as Safe" (GRAS) status and has no known highly allergenic, anti-nutritional or carcinogenic agents associated with it. Maize grain has also demonstrated a superior safety profile in a multitude of animal studies and a human clinical trial [44-51].

Low cost. Production in maize is especially cost-effective. The antigen does not need to be purified; therefore, cost of the active ingredient is exceptionally low. Assuming 1 mg is required for a single dose (100-fold higher than a typical injected dose), the raw material cost would be less than $0.01/dose [53].

Proven commercialization potential. Recombinant proteins produced in maize have been commercialized by our company including trypsin, avidin, endocellulase, exocellulase, and manganese peroxidase [54-57], providing experience for scale-up from laboratory to commercialization and providing a basis for regulatory measures and cost models.

Improvements to Maize Platform: Antigen Levels

One significant technical obstacle to obtaining a plant-produced oral HBV vaccine has been the difficulty of accumulating adequate levels of the subunit vaccine protein (HBsAg) in recombinant hosts. Reports of HBsAg accumulation in edible plant tissue (other than maize) have varied dramatically from banana fruit (0.001 μg/gram fresh weight) to potato (>8 m/gram fresh weight) [31]. Low levels of antigen result in insufficient protein surviving the digestive tract to elicit an immune response. Without purification, there are practical limits to how much tissue can be administered orally, thereby limiting the dose.

Raising the level of accumulation of HBsAg in maize is not a trivial matter as HBsAg, like many other subunit vaccine candidates, is a membrane protein, proteins which are notoriously difficult to express in recombinant systems [58]. However, seed-preferred promoters and expression cassettes that confer high levels of recombinant proteins were developed to improve this situation (U.S. Pat. No. 7,183,109). Using these promoters, we reported HBsAg levels of >50 μg/g [59]. Since then, we have successfully used traditional breeding techniques to raise HBsAg levels to >200 μg/g, a level 20-fold higher than previously reported in potato and used in their human clinical trial [36].

In addition, when constructs are used that confer expression preferentially to the embryo, a second approach, fractionation of the kernel, can be implemented to concentrate the antigen (U.S. Pat. No. 6,504,085). This involves mechanically separating the endosperm and germ (embryo) fractions of the seed. Fractionation can concentrate the HBsAg protein an additional 7-fold, resulting in reported levels of >500 ug/g [20].

With more than an order of magnitude greater levels of HBsAg in maize relative to the highest accumulation in other plant systems, a new situation in oral delivery has developed whereby the antigen concentration should no longer be limiting.

Improvements to Maize Platform: Oil Removal

Initial experiments in which a parenteral primary dose was followed by oral boosting doses using HBsAg germ resulted in an increase in antibody titers in mice for both serum and mucosal antibodies [26]. One concern with these early experiments was whether the high levels of oil in the germ would help or hinder the immune response. As HBsAg is a membrane protein, it is conceivable that membrane lipids in corn germ flour may either increase the ability of the antigen to elicit antibodies by keeping the antigen in proper conformation or decrease its ability by binding to the protein and hiding critical hapten regions.

To study the impact of the higher oil content as a result of using maize germ rather than whole grain, a comparison of full-fat or defatted germ was carried out. The first experiments were done using hexane-extracted material, but hexane is toxic and must be thoroughly removed if the corn material is to be used as a food grade product. Therefore, a food-friendly method using only carbon dioxide ($CO_2$) to remove oil, supercritical fluid extraction (SFE), was also tested [60].

To assess the effect on the immune response, mice were given an injection of a commercial vaccine as a primary dose and orally boosted with full-fat, hexane, or SFE-extracted preparations of HBsAg germ. These treatments were compared to parenteral boosting with the commercial vaccine. The results (FIG. 1) demonstrated that full-fat, hexane and SFE preparations given orally all provided a strong mucosal response, with the SFE preparation inducing the highest titers. This was in contrast to the injected vaccine treatment (Recombivax®) in which no mucosal response could be detected [20] (FIG. 1).

Figure 2:
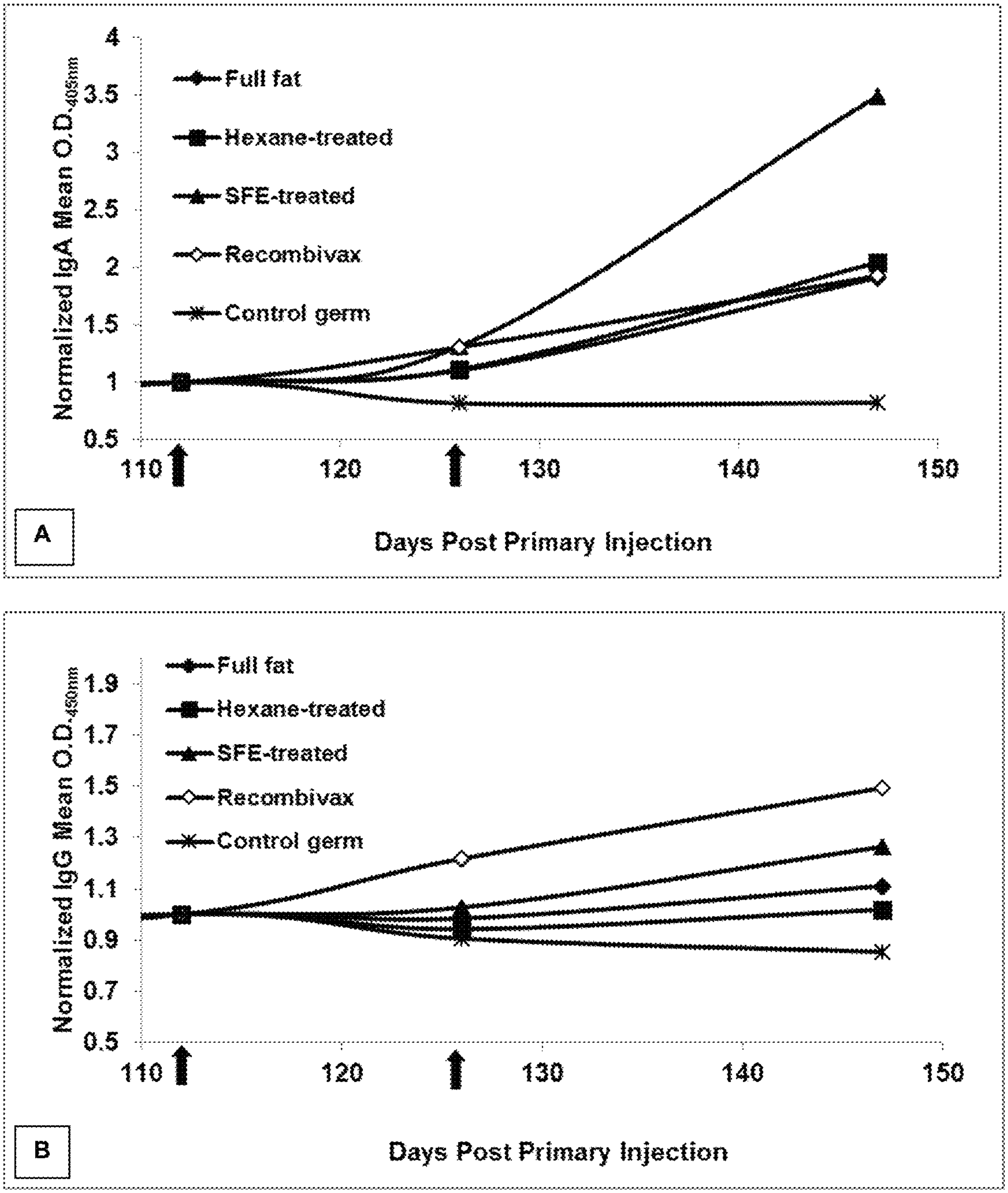
FIG. 2 are graphs showing serum anti-HBsAg in mice. IgA (A panel) and IgG (B panel) response in mice was determined by a sandwich ELISA. Pre-immune-subtracted O.D. values were normalized to pre-boost values for each mouse (O.D. at day n/O.D. at day 112) and means were determined for all mice in a given treatment. Black arrows represent times when mice were orally administered HBsAg wafers or injected with Recombivax® (commercial vaccine). All three preparations of orally delivered HBsAg were able to boost IgG and IgA titers with SFE preparations showing the highest increase. The commercial injected vaccine was used as a positive control and maize material without HBsAg was used as a negative control.

Serum titers were also examined demonstrating that all three preparations of orally delivered HBsAg germ elicited an antibody response. In comparing the IgA in the serum, the SFE preparations provided the highest titers compared to oral full-fat, oral hexane or injected treatments (FIG. 2A). The IgG serum titers were also examined (FIG. 2B) and again all three preparations of maize-HBsAg were able to elicit an IgG response with SFE material showing the highest titers of the orally delivered material and slightly lower titers than the injected vaccine [20]

Another reason to remove oil is to potentially provide greater stability to the transgenic protein. Corn kernels can be stored for years at ambient temperatures while keeping recombinant proteins stable. It was unknown, however, whether fractionation of the kernel to produce an enriched germ fraction with high oil content could lead to oxidation and reduce protein stability. Therefore, we examined the stability of HBsAg in full-fat, hexane and SFE-treated germ flour. Using an ELISA as an indication of stability, all three preparations were examined for stability over elevated temperatures, up to 55° C. The results show that SFE preparations are relatively stable over 1 month even at 55° C. whereas hexane preparations lose antigenicity precipitously at 55° C. and full-fat preparations are unstable, even at 35° C. SFE-treated material also showed the most uniform preparations of virus-like particles (VLPs) [61], the most immunogenic form of HBsAg. These results indicate that SFE provides the most stable environment for HBsAg. Therefore, SFE treatment, a key innovation, improves the immunogenicity and heat stability of the maize material.

Example 2

Improvements to Maize Platform: Wafer Formulation

Defatting germ flour eliminates the problem of oil rancidness over long storage times, allows for blending with control corn flour for precise dosing, and has great temperature stability, making it an ideal starting point for a stable, accurately dosed vaccine. Defatted germ may be transported and stored for several weeks in the hottest of climates, which rarely rise above 50° C. (122° F.), without degrading the antigen.

Eating defatted corn flour is not particularly palatable or practical as a delivery platform; therefore, small wafers were formulated that can be easily consumed. We determined that mixing 2.5 g defatted germ with 1.25 g sugar, adding 0.63 g water to form a wafer in a pellet press, and drying wafers in a vacuum oven provided a convenient method to deliver a precise dosage in a stable palatable form.

Example 3

The above results clearly demonstrate the commercial potential for producing a safe, efficacious, palatable oral vaccine that can eliminate the need for the cold chain. However, there are two key points that need to be addressed for this approach to have practical utility. The first is whether the responses in serum and fecal samples are indicative of protection. Making antibodies does not necessarily mean making protective antibodies. Ideally there would be a small animal model for challenge studies with HBV or a test for neutralizing antibodies. While there is no convenient animal model for hepatitis B infection, there is a WHO International Standard that has been recognized as a biomarker for a protective response. It has been established that 10 mIU/ml antibody in the serum using this standard is sufficient to provide protection and is used reliably due to the primary role of humoral immunity for protection against HBV. As a result, we primarily focus on antibody responses to vaccine administration for our studies.

Figure 3:
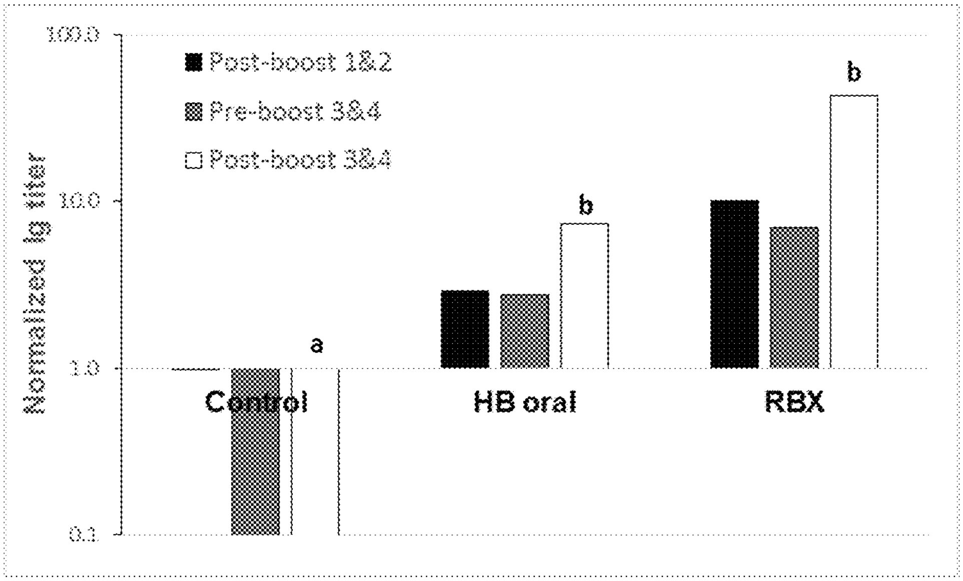
FIG. 3 is a graph showing total Ig response, as determined by the WHO 2nd International Standard. Titers of mice boosted with control germ, HBsAg germ (HB oral), or Recombivax (RBX) were normalized to pre-boost titers (mIU/mL at week n/mIU/mL at pre-boost) and geometric means calculated for each treatment group. Different lower-case letters represent significantly different responses at the terminal bleed (p=0.0005). Both SFE-treated HBsAg material and the commercial vaccine provided an increase in titers well above that indicative of seroprotection. Boosts 1 and 2 were given 3 months post-primary injection (ppi) and Boosts 3 and 4 were given 11 months ppi.

The second point is whether the immune response is transient or involves memory cells that would provide immunity over the long term. The anamnestic response was recently evaluated comparing the orally delivered SFE material in wafers to that of the injected commercial vaccine [19]. In this case, mice were primed with Recombivax®, boosted after three months, and then again after 11 months, or ½ of the life expectancy of a mouse. The results show that both serum and fecal antibodies rapidly increased upon oral boosting at 11 months, indicating that memory cells were involved. To ensure that this was a protective response, the serum titers were also subjected to the WHO standard. Both the injected commercial vaccine and the orally delivered HBsAg wafers showed increased titers using the WHO standard (FIG. 3). The animals were given a total of four boosts. Pre-boost 3 and 4 refers to the titers after boosts 1 and 2. Most importantly, SFE wafers showed serum levels well above that required for seroprotection (mean of 12,755 mIU/ml at the terminal bleed). This was in stark contrast to the wafers that had no HBsAg where titers decreased over this time frame (mean of 71 mIU/mL at the terminal bleed). The injected vaccine also provided an increase in the serum levels, an increase that was not statistically different than the increase in the oral boosting treatment [19].

Results

One aim was to assess the feasibility of improving efficacy of an HBV vaccine. A more potent vaccine may reduce the 3 dose injection regimen to a 2-dose regimen and/or increase antibody titers in traditionally poor responders. One approach is to include an adjuvant, but new, effective, safe adjuvants have been historically difficult to identify, especially for mucosal vaccines. Early studies in potato showed that addition of a bacterial toxin, cholera toxin (CT), could enhance the immunogenicity of an oral HBsAg vaccine in mice [30], but testing of a mutated and less toxic form of another bacterial toxin, heat labile toxin (LT R192G/L211A) showed no adjuvant effect with our oral HBsAg vaccine platform [19].

In an attempt to find a non-toxic adjuvant that is compatible with an oral delivery platform, an inulin-based adjuvant, Advax™, was identified as a likely candidate. Advax™ is a microcrystalline polysaccharide-based adjuvant derived from delta inulin and has a very high safety profile, as attested by several human clinical trials in which Advax™ was co-administered with injected vaccines, including HBsAg [62]. However, Advax™ had not been tested as an adjuvant for orally delivered vaccine candidates.

Figure 4:
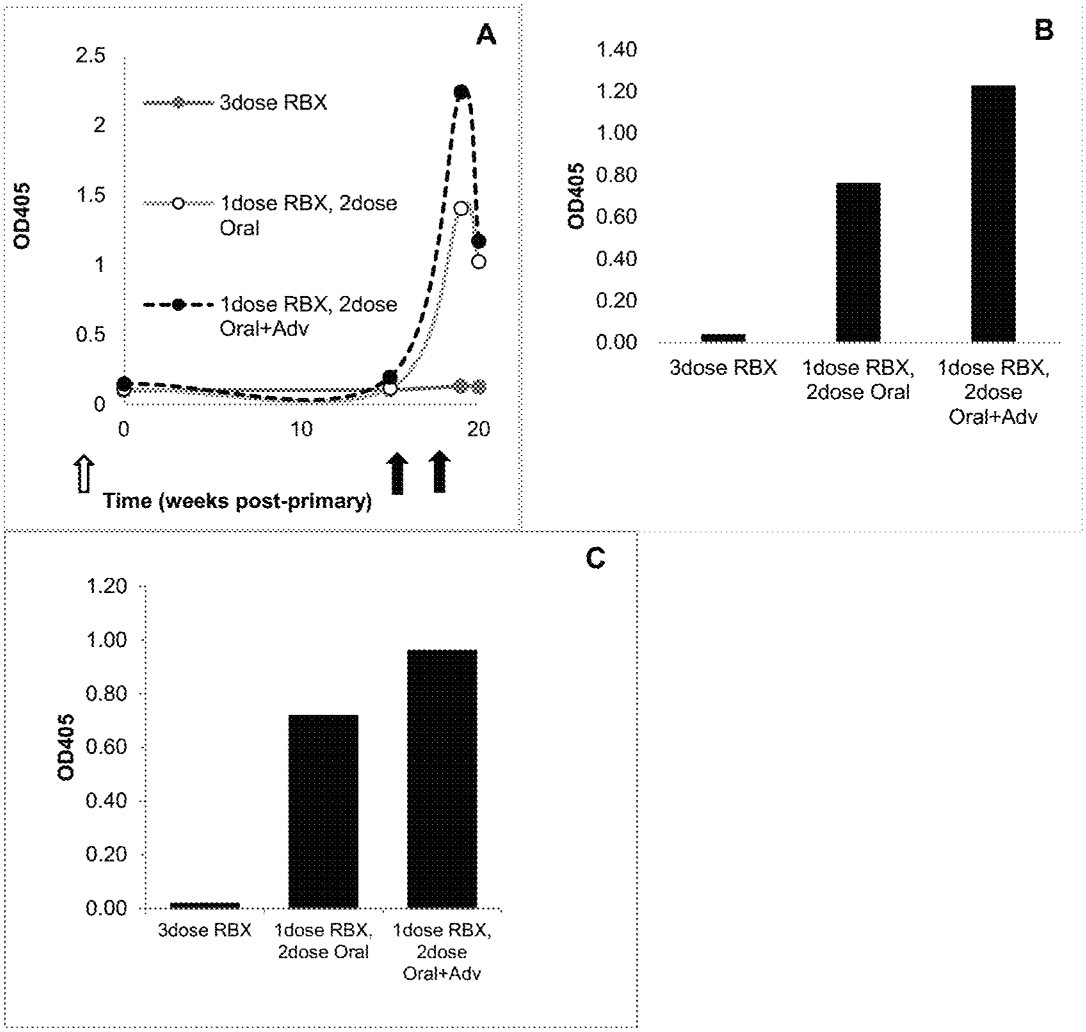
FIG. 4 are graphs showing: anti-HBsAg IgA in A) vaginal washes, B) serum, and C) fecal samples. Mice were injected with 0.25 ug of Recombivax® as a primary dose (white arrow) and boosted twice at days 105 and 119 (black arrows) with i) additional doses of Recombivax® (3dose RBX), ii) oral wafers containing no Advax™ (1dose RBX, 2dose Oral), or iii) oral wafers containing Advax™ (1dose RBX, 2dose Oral+Adv). OD values represent ELISA values read at 405 nm, with samples diluted 1/50 for vaginal washes, 1/250 for serum, and 1/500 for fecal samples. Values for serum and fecal samples were obtained at the terminal bleed (and two days prior to the terminal bleed, respectively.

To test Advax™ as an oral adjuvant, it was formulated with HBsAg maize material to make wafers for oral delivery. Mice were first injected with a commercial vaccine, Recombivax®, as a primary dose, and then boosted orally over two doses with wafers containing 2.5 g maize material, 1.25 g sugar, with or without 50 mg of Advax™. A third treatment of three Recombivax® injections was used as a baseline for commercial vaccine regimens. As seen in FIG. 4, a strong enhancement of vaginal, serum, and fecal IgA was detected in mice consuming Advax™-containing wafers relative to mice fed wafers without Advax™, demonstrating the beneficial effects at both mucosal and systemic sites. Detectable IgA production is notably absent from the injection-only treatment, which has been observed in previous mouse studies, even after 4 boosting doses administered over a one year timeframe [19].

Including Advax™ as an oral adjuvant potentiates the immunologic response by enhancing IgA titers at systemic and vaginal sites, the two sites of most common HBV infection, and represents a key improvement to the oral delivery platform. This sets the precedent for using Advax™ with other orally delivered vaccines.

Figure 5:
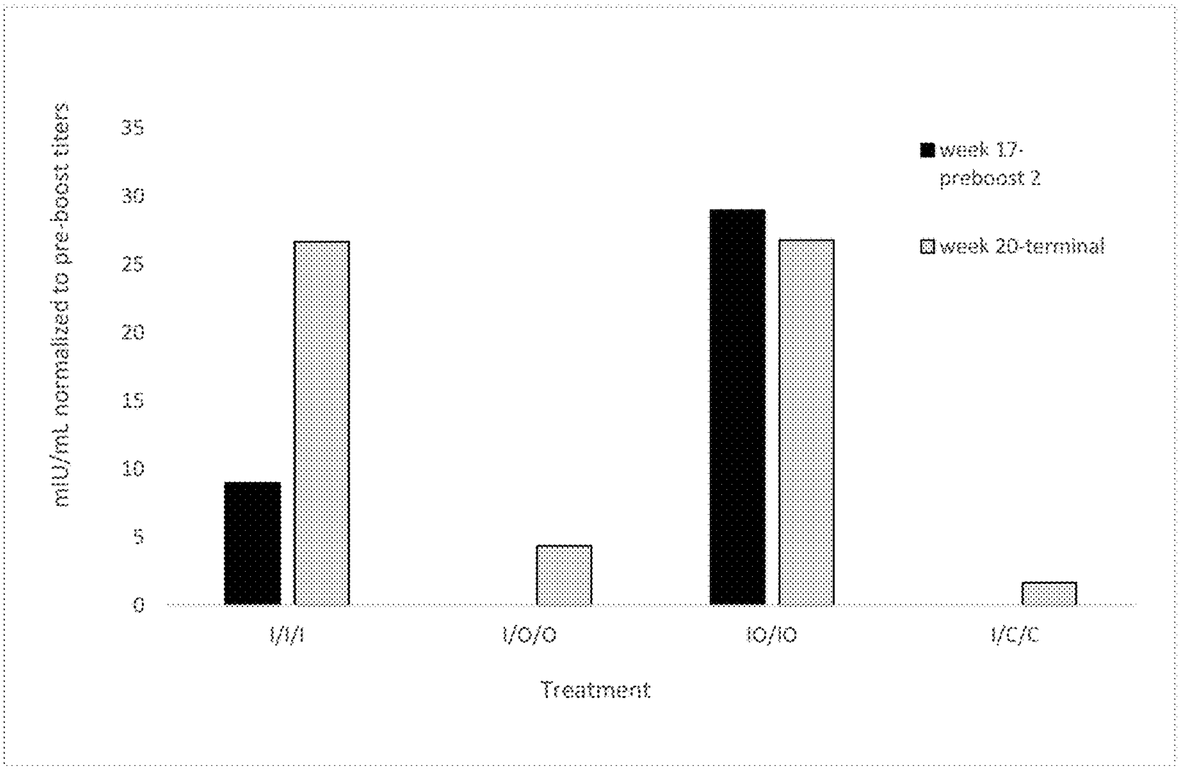
FIG. 5 is a chart showing geometric mean titer of serum anti-HBsAg Ig (mIU/mL) normalized to pre-boost titers.

A second approach to increase the effectiveness of a vaccine is to use a combination of delivery routes. To test this, we combined the commercial injected vaccine with our orally delivered candidate to deliver a "paired" vaccine candidate. All mice were injected on Day 1 with a Recombivax® primary dose. Mice were then divided into four groups receiving, 1) two additional injected boosting doses (baseline for systemic response), 2) two additional oral boosting doses (baseline for mucosal response), 3) a paired oral dose with the injected primary, followed by a single paired injection/oral boosting dose (2 doses total), and 4) two additional control oral boosting doses that contained no HBsAg. Boosting doses were administered on day 105 for all treatments and day 119 when a second boost was administered. The level of serum IgG antibodies induced by 3 injections of Recombivax® was comparable to levels induced by two paired injection/oral doses, as seen in FIG. 5. FIG. 5 shows geometric mean titer of serum anti-HBsAg Ig (mIU/mL) normalized to pre-boost titers. Mice were administered three injected doses (I/I/I), and injected primary followed by two oral boosts (IO/O), and paired injected/oral dose for the primary and first boost (IO/IO), or an injected primary followed by two control oral boosting doses (I/C/C). All mice were tested for mIU/mL at the terminal bleed (week 20, day 133), and treatments I/I/I and IMO were tested at week 17 (day 112), directly preceding the second boost.

Serum IgA levels with the paired vaccine were well above levels seen with the 3-dose injected Recombivax® but lower than the Recombivax® primary followed by 2 doses of oral wafer.

In light of the strong enhancement of IgA provided by Advax™ when it is added to the wafers (FIG. 4), it is our belief that mucosal IgA levels comparable to primary injection with two oral boosts could be achieved in only two doses if an injected vaccine were paired with an oral wafer that contained optimal levels of Advax™. In summary, a paired injection/oral 2-dose vaccine produces a comparable serum IgG response and a superior mucosal and serum IgA response relative to the 3 dose injected vaccine that is presently commercialized.

Example 4

We here describe development of an oral hepatitis B vaccine that is effective at eliciting a response in fewer doses than presently available vaccines on the market. Secondary objectives are to elicit a humoral response at sites important to the prevention of HBV that can provide additional protection.

Assess Stability of the Vaccine Candidate in Adjuvanted Wafers

Figure 6:
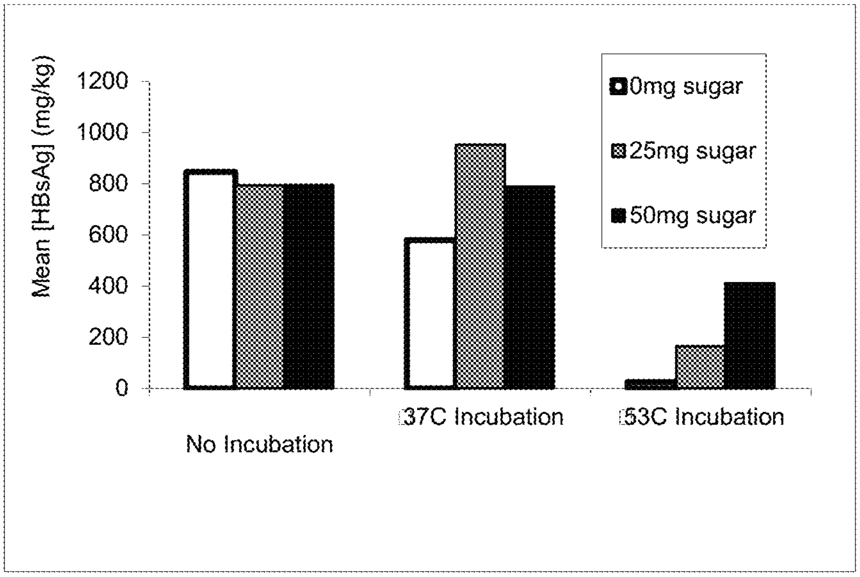
FIG. 6 is a graph showing short-term stability of HBsAg maize under high moisture and high ambient temperature conditions. Maize material (100 mg) was mixed with 0 mg, 25 mg or 50 mg of baker's sugar and 100 uL of purified water. Samples were incubated at 37° C. and 53° C. for 2 hours and HBsAg concentration assessed using an ELISA.

It has been observed that maize antigen exposed to high moisture content and elevated ambient temperatures leads to degradation of HBsAg. This loss of antigen integrity can be inhibited significantly by keeping the moisture content low in the grain and adding baker's sugar to the germ (FIG. 6).

To further reduce the detrimental effects of moisture on the antigen, a dry tableting method is favored over the wet compression method used for previous mouse trials. Dry wafers have been formed using a pilot scale maize/sugar mixture with a single station Natoli RD10A tablet press, resulting in good tensile strength of the wafers, between 1.9 and 2.5 MPa (unpublished results). Due to its compressible nature, Advax™ mixed with maize material should easily form under dry conditions.

Figure 10:
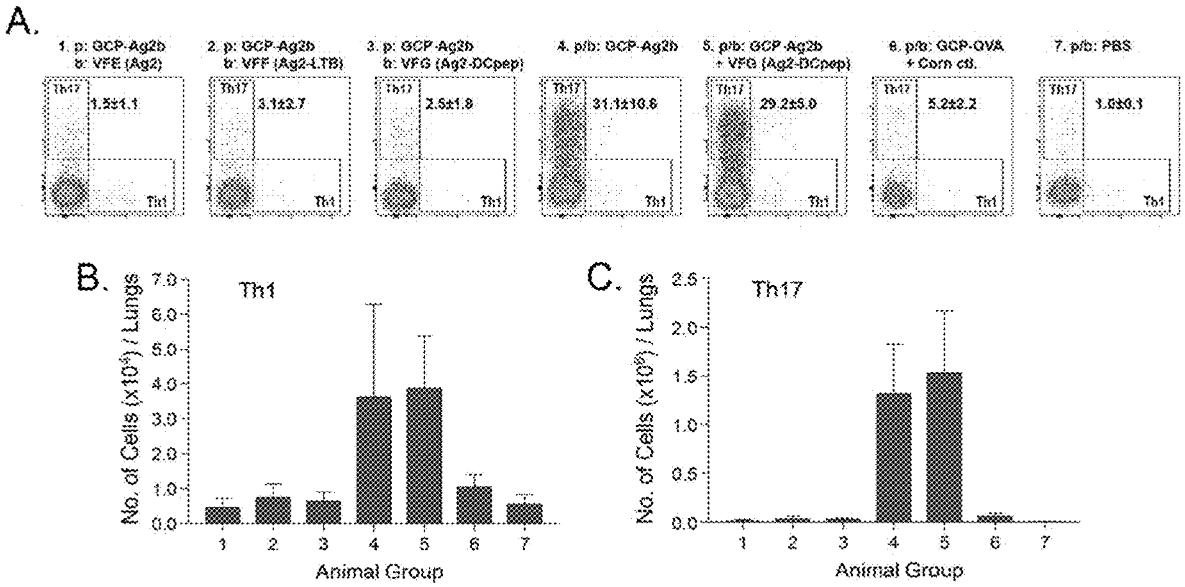
FIG. 10 are images and graphs showing an image (A) and graphs (B) (C) summarizing increase of Th17 cells in the lungs of Ag2-vaccinated mice following FKS challenge. Flow cytometric analysis of IFN-γ- and IL-17A-expressing Th1 and Th17 cells, respectively in lungs of mice that were vaccinated with various Ag2 formulations and challenged with formalin-killed-spherule (FKS) of *Coccidioides posadasii*. Bacterium-expressed recombinant Ag2 encapsulated with glucan-chitin-particles (GCP-Ag2b) and 3 types of maize-derived Ag2 in the form of edible wafers (VFE, VFF and VFG) were used for vaccine priming (p) and/or boosting (b) 3 times at 2 weeks apart. GCP-OVA, wafer contained no Ag2 (corn ctl.) and PBS alone were used for mock vaccination. The percentages of gated, specific IL-17A producing cells per lung organ (panel A) and the numbers of Th1 (CD4+IFN-γ+; panel B) and Th17 (CD4+IL-17A+; panel C) cells, were determined by intracellular cytokine staining 7 days post FKS challenge.

Inulin is used to stabilize proteins [63] and crystalline inulin (Advax™) may also be able to stabilize proteins. In order to test the dry tableting characteristics of Advax™ and possible stabilizing effects, different amounts of Advax™ can be added to wafers in the presence or absence of sugar. Wafers can be made with 2.5 g delipidated ground maize material and combined with:

a) 0 mg, 50 mg, 150 mg, and 500 mg Advax™, no sugar
b) 0 mg, 50 mg, 150 mg, and 500 mg Advax™+sugar so that Advax™+sugar makes up 25% of germ weight
c) 0 mg, 50 mg, 150 mg, and 500 mg of Advax™+sugar so that Advax™+sugar makes up 50% of germ weight The wafers can then be subjected to accelerated degradation conditions, as used in FIG. 10 (high moisture and high ambient temperatures for two hours). It is conceivable that Advax™, an oligosaccharide, will stabilize the antigen, perhaps more efficiently than sugar, therefore different total amounts of sugar+Advax™ have been included in this experiment. HBsAg integrity can be assessed by ELISA and used to identify the formulation with the greatest antigen stability. Formulations that produce the preferred characteristics for wafers and the highest HBsAg integrity with the lowest level of sugar will be used in Task 6 in order to obtain the highest possible concentration of antigen in the wafers.

The process is expected to identify formulated wafers with maximal antigen stability under accelerated degradation conditions, as determined by ELISA, and identify formulations with favorable tableting characteristics/

REFERENCES

1. Ott, J. J., et al., *Global epidemiology of hepatitis B virus infection: New estimates of age-specific HBsAg seroprevalence and endemicity*. Vaccine, 2012. 30(12): p. 2212-2219.

2. Keating, G. M. and S. Noble, *Recombinant hepatitis B vaccine (Engerix-B (R))—A review of its immunogenicity and protective efficacy against hepatitis B. Drugs,* 2003. 63(10): p. 1021-1051.

3. Wasley, A., et al., *The Prevalence of Hepatitis B Virus Infection in the United States in the Era of Vaccination*. Journal of Infectious Diseases, 2010. 202(2): p. 192-201.

4. Chen, D.-S., *Hepatitis B vaccination: The key towards elimination and eradication of hepatitis B*. Journal of Hepatology, 2009. 50(4): p. 805-816.

5. Ahishali, E., et al., *Response to hepatitis B vaccination in patients with celiac disease*. Digestive diseases and sciences, 2008. 53(8): p. 2156-2159.

6. Leonardi, S., et al., *Hepatitis B vaccination failure in celiac disease: Is there a need to reassess current immunization strategies?* Vaccine, 2009. 27(43): p. 6030-6033.

7. Vida Perez, L., et al., *Eficacia de la vacuna contra el virus de la hepatitis B en pacientes con enfermedad inflamatoria intestinal*. Medicina clinica, 2009. 132(9): p. 331-335.

8. Roome, A. J., et al., *Hepatitis B vaccine responsiveness in Connecticut public safety personnel*. JAMA: the journal of the American Medical Association, 1993. 270(24): p. 2931.

9. van den Berg, R., I. van Hoogstraten, and M. van Agtmael, *Non-responsiveness to hepatitis B vaccination in HIV seropositive patients; possible causes and solutions*. AIDS reviews, 2009. 11: p. 157-64.

10. Tohme, R. A., et al., *Evaluation of hepatitis B vaccine immunogenicity among older adults during an outbreak response in assisted living facilities*. Vaccine, 2011.

11. Mahoney, F. J., et al., *Progress toward the elimination of hepatitis B virus transmission among health care workers in the United States*. Archives of Internal Medicine, 1997. 157(22): p. 2601.

12. Dannetun, E., et al., *Coverage of hepatitis B vaccination in Swedish healthcare workers*. Journal of Hospital Infection, 2006. 63(2): p. 201-204.

13. Simard, E. P., et al., *Hepatitis B vaccination coverage levels among healthcare workers in the United States,* 2002-2003. Infection control and hospital epidemiology, 2007. 28(7): p. 783-790.

14. Fabrizi, F., et al., *Intradermal versus intramuscular hepatitis b re-vaccination in non-responsive chronic dialysis patients: a prospective randomized study with cost-effectiveness evaluation*. Nephrology Dialysis Transplantation, 1997. 12(6): p. 1204-1211.

15. Kalchiem-Dekel, O., et al., *Efficacy and long-term durability of intradermal recombinant hepatitis B virus vaccine among intramuscular vaccine nonresponders—a prospective study in healthcare personnel*. Journal of Gastroenterology and Hepatology, 2015.

16. Yousaf, F., et al., *Systematic review of the efficacy and safety of intradermal versus intramuscular hepatitis B vaccination in end-stage renal disease population unresponsive to primary vaccination series*. Renal Failure, 2015(Aug.10): p. 1-9.

17. Lappalainen, S., et al., *Protection against live rotavirus challenge in mice induced by parenteral and mucosal delivery of VP6 subunit rotavirus vaccine*. Archives of Virology, 2015: p. 1-4.

18. Wu, H., et al., *Immunization of chickens with VP2 protein of infectious bursal disease virus expressed in Arabidopsis thaliana*. Avian Diseases, 2004. 48(3): p. 663-668.

19. Hayden, C. A., et al., *Oral delivery of wafers made from HBsAg-expressing maize germ induces long-term immunological systemic and mucosal responses*. Vaccine, 2015. 33: p. 2881-2886.

20. Hayden, C. A., et al., *Supercritical fluid extraction provides an enhancement to the immune response for orally-delivered hepatitis B surface antigen*. Vaccine, 2014. 32(11): p. 1240-1246.

21. Cuburu, N., et al., *Sublingual immunization induces broad-based systemic and mucosal immune responses in mice*. Vaccine, 2007. 25(51): p. 8598-610.

22. Song, J. H., et al., *Sublingual vaccination with influenza virus protects mice against lethal viral infection*. Proceedings of the National Academy of Sciences of the United States of America, 2008. 105(5): p. 1644-1649.

23. Brandtzaeg, P. and F. E. Johansen, *Mucosal B cells: phenotypic characteristics, transcriptional regulation, and homing properties. Immunological reviews,* 2005. 206(1): p. 32-63.

24. Czerkinsky, C. and J. Holmgren, *Mucosal delivery routes for optimal immunization: targeting immunity to the right tissues, in Mucosal Vaccines: Modern Concepts, Strategies, and Challenges*, P. Kozlowski, Editor. 2012, Springer: Heidelberg. p. 1-18.

25. CDC, *A comprehensive immunization strategy to eliminate transmission of hepatitis B virus infection in the United States*. MMWR, 2006. 55(RR-16): p. 1-33.

26. Hayden, C. A., et al., *Bioencapsulation of the hepatitis B surface antigen and its use as an effective oral immunogen*. Vaccine, 2012. 30(19): p. 2937-2942.

27. Gao, Y., et al., *Oral immunization of animals with transgenic cherry tomatillo expressing HBsAg*. World Journal of Gastroenterology, 2003. 9(5): p. 996-1002.

28. Joung, Y., et al., *Expression of the hepatitis B surface S and preS2 antigens in tubers of Solanum tuberosum*. Plant Cell Reports, 2004. 22(12): p. 925-930.

29. Kapusta, J., et al., *A plant-derived edible vaccine against hepatitis B virus*. The FASEB Journal, 1999. 13(13): p. 1796-1799.

30. Kong, Q., et al., *Oral immunization with hepatitis B surface antigen expressed in transgenic plants*. Proceedings of the National Academy of Sciences, USA, 2001. 98(20): p. 11539-11544.

31. Kumar, G., T. Ganapathi, and V. Bapat, *Production of hepatitis B surface antigen in recombinant plant systems: an update*. Biotechnology Progress, 2007. 23(3): p. 532-539.

32. Lou, X.-M., et al., *Expression of the human hepatitis B virus large surface antigen gene in transgenic tomato plants*. Clinical and Vaccine Immunology, 2007. 14(4): p. 464-469.

33. Pniewski, T., et al., *Low-dose oral immunization with lyophilized tissue of herbicide-resistant lettuce expressing hepatitis B surface antigen for prototype plant-derived vaccine tablet formulation*. Journal of Applied Genetics, 2011. 52(2): p. 125-136.

34. Shchelkunov, S. N., et al., *Immunogenicity of a novel, bivalent, plant-based oral vaccine against hepatitis B and human immunodeficiency viruses*. Biotechnology Letters, 2006. 28(13): p. 959-967.

35. Youm, J.-W., et al., *Oral immunogenicity of potato-derived HBsAg middle protein in BALB/c mice*. Vaccine, 2007. 25(3): p. 577-584.

36. Thanavala, Y., et al., *Immunogenicity in humans of an edible vaccine for hepatitis B*. Proceedings of the National Academy of Sciences, USA, 2005. 102(9): p. 3378-3382.

37. Huang, Z., et al., *High-yield rapid production of hepatitis B surface antigen in plant leaf by a viral expression system*. Plant Biotechnology Journal, 2008. 6(2): p. 202-209.

38. Bailey, M. R., *A model system for edible vaccination using recombinant avidin produced in corn seed, in Biochemistry*. 2000, Texas A&M: College Station. p. 81.

39. Egelkrout, E., et al., *Enhanced Expression Levels of Cellulase Enzymes Using Multiple Transcription Units*. BioEnergy Research, 2013. 6(2): p. 699-710.

40. Hood, E. E., et al., *Criteria for high-level expression of a fungal laccase gene in transgenic maize*. Plant Biotechnology Journal, 2003. 1(2): p. 129-140.

41. Hood, E. E., et al., *Manipulating corn germplasm to increase recombinant protein accumulation*. Plant Biotechnology Journal, 2012. 10(1): p. 20-30.

42. Arakawa, T. and S. N. Timasheff, *Stabilization of protein structure by sugars*. Biochemistry, 1982. 21(25): p. 6536-6544.

43. Boisen, S., *Protease inhibitors in cereals*. Acta Agriculturae Scandinavica, 1983. 33(4): p. 369-381.

44. Guerrero-Andrade, O., et al., *Expression of the Newcastle disease virus fusion protein in transgenic maize and immunological studies*. Transgenic Research, 2006. 15(4): p. 455-463.

45. Lamphear, B. J., et al., *A corn-based delivery system for animal vaccines: an oral transmissible gastroenteritis virus vaccine boosts lactogenic immunity in swine*. Vaccine, 2004. 22(19): p. 2420-2424.

46. Lamphear, B. J., et al., *Delivery of subunit vaccines in maize seed*. J Control Release, 2002. 85(1-3): p. 169-180.

47. Loza-Rubio, E., et al., *Induction of a protective immune response to rabies virus in sheep after oral immunization with transgenic maize*. Vaccine, 2012. 30(27): p. 5551-5556.

48. Streatfield, S. J., et al., *Plant-based vaccines: unique advantages*. Vaccine, 2001. 19(17-19): p. 2742-2748.

49. Streatfield, S. J., et al., *Corn as a production system for human and animal vaccines*. Vaccine, 2003. 21(7-8): p. 812-815.

50. Streatfield, S. J., et al., *Development of an edible subunit vaccine in corn against enterotoxigenic strains of Escherichia coli*. In Vitro Cellular & Developmental Biology-Plant, 2002. 38(1): p. 11-17.

51. Tacket, C. O., et al., *Immunogenicity of recombinant LT-B delivered orally to humans in transgenic corn*. Vaccine, 2004. 22(31-32): p. 4385-4389.

52. Fischer, R., et al., *Plant-based production of biopharmaceuticals*. Current Opinion in Plant Biology, 2004. 7(2): p. 152-158.

53. Howard, J. A. and E. Hood, *Bioindustrial and biopharmaceutical products produced in plants*. Advances in Agronomy, 2005. 85: p. 91-124.

54. Hood, E. E., et al., *Commercial production of avidin from transgenic maize: characterization of transformant, production, processing, extraction and purification*. Molecular Breeding, 1997. 3(4): p. 291-306.

55. Witcher, D. R., et al., *Commercial production of β-glucuronidase (GUS): a model system for the production of proteins in plants*. Molecular Breeding, 1998. 4(4): p. 301-312.

56. Woodard, S. L., et al., *Maize (Zea mays)-derived bovine trypsin: characterization of the first large-scale, commercial protein product from transgenic plants*. Biotechnology and Applied Biochemistry, 2003. 38(2): p. 123-130.

57. Zhong, G.-Y., et al., *Commercial production of aprotinin in transgenic maize seeds*. Molecular Breeding, 1999. 5(4): p. 345-356.

58. Grisshammer, R., *Understanding recombinant expression of membrane proteins*. Current Opinion in Biotechnology, 2006. 17(4): p. 337-340.

59. Hayden, C. A., et al., *Production of highly concentrated, heat-stable hepatitis B surface antigen in maize*. Plant Biotechnology Journal, 2012. 10(8): p. 979-984.

60. Brunner, G., *Supercritical fluids: technology and application to food processing*. Journal of Food Engineering, 2005. 67(1): p. 21-33.

61. Shah, S., et al., *Biochemical and biophysical characterization of maize-derived HBsAg for the development of an oral vaccine*. Archives of Biochemistry and Biophysics, 2015. 588: p. 41-49.

62. Petrovsky, N. and P. D. Cooper, *Advax™, a novel microcrystalline polysaccharide particle engineered from delta inulin, provides robust adjuvant potency together with tolerability and safety*. Vaccine, 2015. 33(44): p. 5920-5926.

63. Mensink, M. A., et al., *Inulin, a flexible oligosaccharide. II: Review of its pharmaceutical applications*. Carbohydrate polymers, 2015. 134: p. 418-428.

64. Mangold, C., et al., *Analysis of intermolecular disulfide bonds and free sulfhydryl groups in hepatitis B surface antigen particles*. Archives of Virology, 1997. 142(11): p. 2257-2267.

65. Mangold, C. M., et al., *Secretion and antigenicity of hepatitis B virus small envelope proteins lacking cysteines in the major antigenic region*. Virology, 1995. 211(2): p. 535-543.

66. Vyas, G., K. Rao, and A. Ibrahim, *Australia antigen (hepatitis B antigen): a conformational antigen dependent on disulfide bonds*. Science (New York, N.Y.), 1972. 178(67): p. 1300-1301.

67. FDA. *Water activity (aw) in foods*. 1984 [cited 2013 Oct. 8]; Available from: world wide web.fda.gov/ICECI/Inspections/InspectionGuides/InspectionTechnicalGuides/ucm072 916.htm.

68. FAO/WHO, *Evaluation of certain mycotoxins in food. Fifty-sixth report of the joint FAO/WHO Expert Committee on Food Additives, in WHO Technical Report Series*. 2001, World Health Organization: Geneva, Switzerland.

69. FDA. *Guidance for Industry: Action Levels for Poisonous or Deleterious Substances in Human Food and Animal Feed*. 2000 Jan. 9, 2013]; Available from: world wide web.fda.gov/Food/GuidanceRegulation/GuidanceDocumentsRegulatoryInformation/ChemicalContaminants-MetalsNaturalToxinsPesticides/ucm077969.htm.

70. FDA. *Mycotoxins in Domestic and Imported Foods*. 2008 [cited 2015 Feb. 23]; Available from: world wide web.fda.gov/downloads/Food/ComplianceEnforcement/UCM073294.pdf.

71. Moldoveanu, Z. and K. Fujihashi, *Collection and processing of external secretions and tissues of mouse origin, in Mucosal Immunology*, J. Mestecky, et al., Editors. 2015, Academic Press: Boston, Mass. p. 2355-2368.

72. Hsu, D. C., *Janeway's Immunobiology*. Shock, 2008. 29(6): p. 770.

73. Powell, M., et al., *Effects of subchronic exposure to transgenic papayas (Carica papaya L.) on liver and kidney enzymes and lipid parameters in rats*. Journal of the science of food and agriculture, 2008. 88(15): p. 2638-2647.

Example 5

In the following experiments a vaccine was prepared using a nucleotide sequence encoding the *Coccidioides* antigen 2 polypeptide. Infection with *Coccidioides* causes the disease Valley Fever. Humans and other mammals living in, or traveling to, the endemic regions inhale the airborne *Coccidioides* spores through the nasal passage, which can lead to coccidioidomycosis, otherwise known as San Joaquin Valley Fever. Attack rates are estimated to be 11% for Caucasians, 54% for African-Americans, 67% for Filipinos, and 36% for Asians4. While 60% of infections are asymptomatic, the remaining 40% result in pulmonary disease that mimics flu-like symptoms.

Materials and Methods

Construct Design

Figure 7:
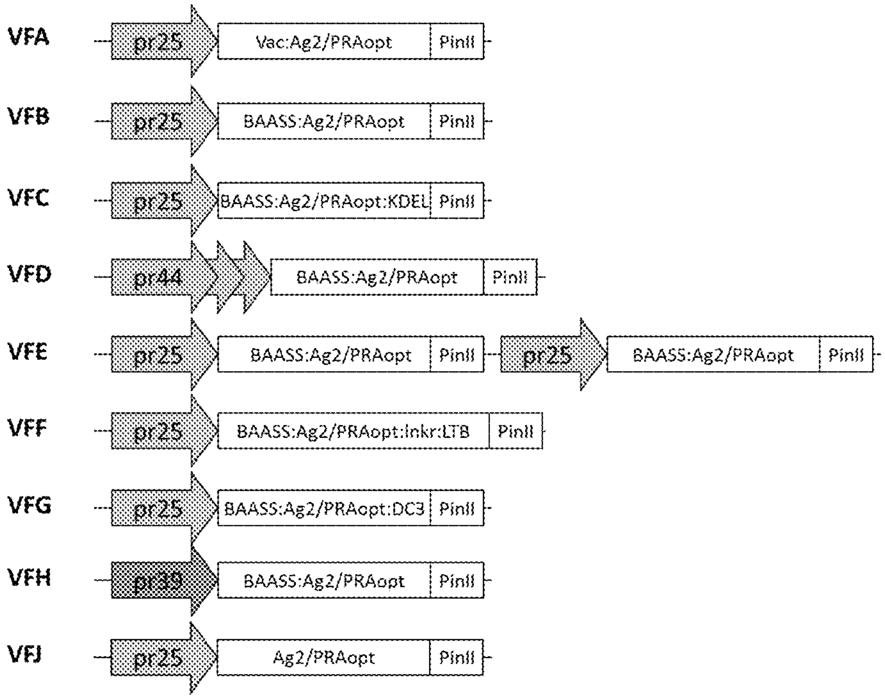
FIG. 7 is a graphic showing a schematic representations of rAg2 expression constructs. Nine plasmid constructs were designed to express recombinant Ag2 in maize. Tissue-preferential maize promoters (Pr25:seed embryo, Pr44:seed embryo, and Pr39:endosperm) were used to drive high Ag2 gene transcription and subsequent high yield of protein production. In various constructs, cellular/organelle-targeting sequences were added (Vac:vacuole, BAASS:cell wall) and C-terminus (KDEL:ER) to the codon-optimized Ag2 (Ag2opt). Immune-modulators, a heat labile enterotoxin B subunit (LTB) and a dendritic cell targeting sequence (DC-pep) were fused to the C-terminus of Ag2opt as indicated for VFF and VFG constructs, respectively. Untranslated 3' region of a potato protease inhibitor II (pinII) was added to all constructs as a transcriptional termination element to enhance mRNA stability.

The full-length Ag2 sequence (GenBank accession U39835) was codon-optimized for expression in maize, predicted splice sites and instability elements were screened for and removed, and a valine was placed directly preceding the Ag2 sequence in order to improve stability of the protein. All constructs contained promoters that preferentially accumulate protein in maize seed. Construct VFA (FIG. 7) was assembled with a 3 kb globulin 1 promoter sequence[20], which acts to produce protein in the embryo portion of the seed. The promoter was followed by a vacuolar targeting signal sequence, derived from a barley aleurain[21]. Construct VFB was constructed in the same manner as VFA but contained the barley alpha amylase signal sequence (BAASS) in order to target the protein to the cell wall. Construct VFC contained a third targeting signal, a combination of the BAASS at the N-terminus and a KDEL sequence at the C-terminus in order to target the protein to the endoplasmic reticulum (ER). A fourth construct, VFD, contained an enhanced globulin 1 promoter with three copies of the 5'-most 1745 bp promoter[22]. VFE was constructed with the same components as VFB with two copies of the transcription unit placed in tandem in a head-to-tail orientation. VFF was assembled in the same manner as the VFB construct, with a linker sequence connecting the Ag2 C-terminal sequence to the LTB N-terminal sequence (GenBank accession M17874). VFG also contained the same components as VFB, with the addition of a dendritic cell targeting sequence, DCpep[16] at the Ag2 C-terminus. VFH was modeled after VFB, but contained a promoter that expressed preferentially in the endosperm, the 27 kDa gamma-zein promoter[23]. Finally, transcription elements in VFJ were the same as in VFA, to the exclusion of a plant-derived targeting signal. Only the original fungal endogenous Ag2 targeting signal was included in this construct. All DNA construct coding sequences were followed by a potato protease inhibitor II (pinII) 3'-untranslate region for enhancing mRNA stability[24], and a glufosinate resistance gene which is a maize optimized phosphinothricin N-acetyltransferase (pat) gene from *Streptomyces viridiochromogenes*[25] for selection of putative plant transformants. Ag2 transgenic constructs used for *E. coli* expression and purification were conducted as described previously[9]

Maize Transformation and Seed Propagation

Constructs VFA to VFJ were transformed into *Agrobacterium tumefaciens* and maize, as described previously[26]. Selection of transformed lines was done by using bialaphos and propagated as described previously[25,27]. T1 seed was generated by crossing the ears of the transformed (T0) plants with the pollen of the transformation germplasm, HiII. T2 seed were generated by self-pollination of the T1 plants.

Purification of Ag2 from Bacteria and Production of Antibodies

*E.coli*-derived Ag2 was purified as previously described[9], with some modifications. In brief, *E. coli* containing the Ag2-expression plasmid were grown at 37° C. overnight in LB medium with antibiotic. This transformed bacterium overexpressed a thioredoxin-His(6×)-Ag2 fusion protein with a thrombin cleavage site between His(6×) and Ag2. The seed culture was used to inoculate two 1 L flasks containing 250 mL MagicMedia (ThermoFisher Scientific, Waltham, Mass.) with antibiotic and grown overnight. The cell pellets were harvested, ground with liquid nitrogen, resuspended in PBS, and treated with DNAseI. The pellet was then resuspended in 8M urea and centrifuged to collect the supernatant. The supernatant was then adjusted to 2M urea and the extract was loaded onto a Ni-NTA His-bind resin (Novagen). After washing with the same buffer, the column was treated with thrombin and the Ag2 was released from the column. The Ag2 in the eluate was confirmed by Coomassie gel electrophoresis. This material was then sent to Pacific Immunology to make rabbit polyclonal antibodies. The final bleed was used for all analysis.

Quantitation of Ag2 from Maize

Protein was extracted from either single T1 seeds or 100 mg±5 mg of ground T2 50-seed bulk material using 1 mL PBS+1% TritonX100 extraction buffer. Six single T1 seeds were sampled from each ear while 50-seed T2 bulks were assayed in duplicate. Percent total soluble protein in T1 seed were determined by measuring total soluble protein using a Bradford Assay. Estimated mg/kg were assessed by weighing the combined 6 seeds and calculating a mean weight for each seed. Antigen in the extract was detected using custom polyclonal anti-Ag2 antibodies that were generated in rabbit using purified Ag2 from *E. coli*[9]. A sandwich ELISA was developed in which the terminal bleed rabbit serum was used to coat ELISA plates. Plates were blocked with PBS+3% BSA, washed with PBS, and detection antibody was applied in PBS+3% BSA. Detection antibody was generated by purifying the serum antibody on a protein A column and biotinylating the resultant fraction of purified antibody (Innova Biosciences, Cambridge, UK). Streptavidin-AP and pNPP tablets were used to detect antibody binding to Ag2. The recombinant *E coli*-purified protein was used as a standard curve on all ELISAs.

Purification of Maize-derived Ag2.

Ag2 was extracted from ground maize material from VFG lines using PBS+1% TritonX-100. After extraction for 30 minutes on ice, the suspension was centrifuged and filtered to remove cell debris. The extracts were affinity purified using custom polyclonal antibodies bound to an AminoLink resin (Thermo Fisher Scientific, Waltham, Mass.) and elution of the Ag2 protein with glycine buffer pH 3 followed immediately with buffer neutralization. SDS-PAGE was performed using 10% gels (Bio-Rad #4561033) run with Tris/glycine/SDS running buffer (Bio-Rad, #1610732). For Western blotting, two gels were run simultaneously, one stained using Coomasie Blue for molecular weight analysis and the other transferred to a Nitrocellulose membrane (Thermo Fisher Scientific) using the iBlot 2 system (Invitrogen) for immunoblotting detection. Custom rabbit polyclonal anti-Ag2 primary antibody was then applied to the nitrocellulose membrane, followed by AP-conjugated goat anti-rabbit IgG secondary antibody (Jackson ImmunoResearch #111-055-003, West Grove, Pa.), and BCIP/NBT liquid substrate (Sigma #B1911, St. Louis, Mo.) for Ag2 band visualization.

Preparation of Vaccine Candidates

Maize grain was ground into flour and formed into wafer-like tablets by adding water and confectioner's ultrafine sugar and drying the wafers in a vacuum oven as described previously[28] In brief, maize Ag2 wafers were produced from a mixture of 2.5 g±0.1 g ground T1 seed, 1.85 g±0.05 g of confectioner's sugar, and 0.6 g±0.05 g of water. They were formed in a custom hand press and dried at 55° C.±4° C. in a vacuum oven at 21.5" Hg±0.5" Hg in less than one hour. Control wafers were produced using ground non-transgenic maize material (G909) obtained from Grain Processing Corporation (Muscatine, Iowa) using the same method of wafer formation and drying as for active ingredient wafers.

GCP particles used for injection were loaded with *E. coli*-purified Ag2, as described previously[17,29]. Each dose consisted of 200 μg GCPs, 1 μg Ag2, and 25 μg mouse serum album. Ovalbumin (1 μg) was used as a positive control for loading of the particles. Maize-produced Ag2 GCP particles for immunization was made from purified material using seed from the VFG construct (Ag2:DCpep). The concentration of maize-produced Ag2 was much lower (~10% of that used from bacterial-produced Ag2) due to limitations in the amount of seed available at the time. Efficiency of protein loading was confirmed by SDS-PAGE.

Mouse Studies

Formalin-killed spherule (FKS) challenge study: Ten BALB/c mice, 5 males and 5 females, were assigned to each treatment. Immediately preceding the first day of each dose, all mice were fasted overnight. Treatment 1 consisted of a subcutaneous (sc) injection of 1 of *E. coli*-derived Ag2-loaded into 200 μg GCPs on day 0, and 15 g of oral VFE wafers for boosting doses delivered on days 14, 28, and 42. Mice were fed on wafers ad libitum, and wafers were administered for three consecutive days, 5 g per day per mouse, for each dose. Treatments 2 and 3 were the same as Treatment 1 except VFF and VFG wafers were fed to mice, respectively. Treatment 4 consisted of Ag2 GCP particle injection on days 0, 14, 28, and 42. Treatment 5 consisted of a combination of injected and VFG oral dose on all dosing days. Treatment 6 was control GCP particles and control wafers administered on all dosing days. Mice in Treatment 7 were injected with saline on all dosing days. Mice were then challenged with formalin-killed *Coccidioides* spherules on day 63 and sacrificed on day 70 to look at the T cell response in the lung and spleen. Blood was collected on days 0, 28, 54, and 70 to test for antibody production.

Live arthroconidia challenge study: Treatment group size, mouse breed, and gender distribution was as in Mouse study 1. All doses were initiated on day 0 and 14 (one primary dose and one boosting dose). Mice were challenged with intranasal delivery of approximately 100 viable arthroconidia per mouse, carried out on day 42. Lung colony forming units (CFUs) were analyzed on day 56.

Anti-Ag2 Antibody Detection

Induction of anti-Ag2 specific serum IgG and IgA following vaccination was assessed using a sandwich ELISA similar to that previously described[30]. In brief, ELISA plates were coated with *E. coli*-purified Ag2 in carbonate buffer at pH 9.6. Serum samples were diluted 1:100 for IgG and 1:30 for IgA. AP-conjugated anti-mouse IgG (Jackson Immunoresearch Laboratories, cat #115-055-008) or AP-conjugated anti-mouse IgA (Abcam, cat #134422) were used to detect IgG and IgA, respectively. A pNPP solution was then used to visualize results and read at an OD of 405 nm.

Splenocyte Recall Assay/IFN-Gamma and IL17A ELISPOT

Following terminal bleeds, spleens were dissected from 4 mice in each treatment and analyzed for cytokine production using a T-cell recall assay, as described previously[29]. Dissections were done in duplicate (spleens removed from an additional 4 mice in each group) to increase robustness of the analysis. IFN-γ and IL-17A cytokines were analyzed as indicators of Th1 and Th17 responses, respectively. Statistically significant differences between cytokine production in parenterally and orally vaccinated mice were determined using a Student t-test, as previously described[29].

Intracellular Cytokine Staining

Intracellular cytokine staining assays were conducted to determine the numbers of IFN-γ- and IL-17-producing $CD4^+$ T cells in lungs at 9 and 14 days post-challenge. Pulmonary leukocytes were isolated, as previously reported ([31]). Briefly, aliquots of pulmonary leukocytes were stimulated with anti-CD3 and CD28 in the presence of GolgiStop™ in 10% FBS complemented RPMI 1640 for 4 hours at 37° C. Permeabilized cells were stained with selected fluorochrome-conjugated monoclonal antibodies specific for CD4, CD8, IFNγ, or IL-17A to determine absolute numbers of the specific cytokine-producing $CD4^-$ T cells. The leukocytes were gated for $CD4^+$ T cells and their levels of cytokine expression were determined. The absolute numbers of the specific cytokine-producing $CD4^+$ T cells relative to the total lung-infiltrated leukocytes per lung homogenate was calculated by multiplying the percentage of each gated population by the total number of viable pulmonary leukocytes determined by hemocytometer counts, as previously reported. Student-Newman-Keuls test, a type of ANOVA statistical analysis for all pairwise comparisons, was used to analyze percentages and numbers of specific cytokine-producing T cells in lungs of mice, as previously reported.

CFU Quantification

Lung fungal burden was assessed at day 56, 2 weeks post-challenge, as CFU/lung was evaluated as previously described[32] and the Mann-Whitney U test was applied for statistical analysis, as previously described[9].

Results

Accumulation of Ag2 in Maize

Previous work with other recombinant proteins has demonstrated several factors that influence accumulation in the host tissue including; optimized coding sequence, tissue-preferred promoters and subcellular targeting signals. In addition, carrier proteins have been shown to increase the immune response for some antigens. The additional sequence from the carrier protein also has the potential to influence the accumulation of the protein in the host. Therefore, the various seed-preferred constructs shown in FIG. 1 were created to test for Ag2 accumulation. Each construct was transformed into maize and seed harvested for evaluation. A total of 63 transformation events representing the various constructs were harvested.

Figure 8:
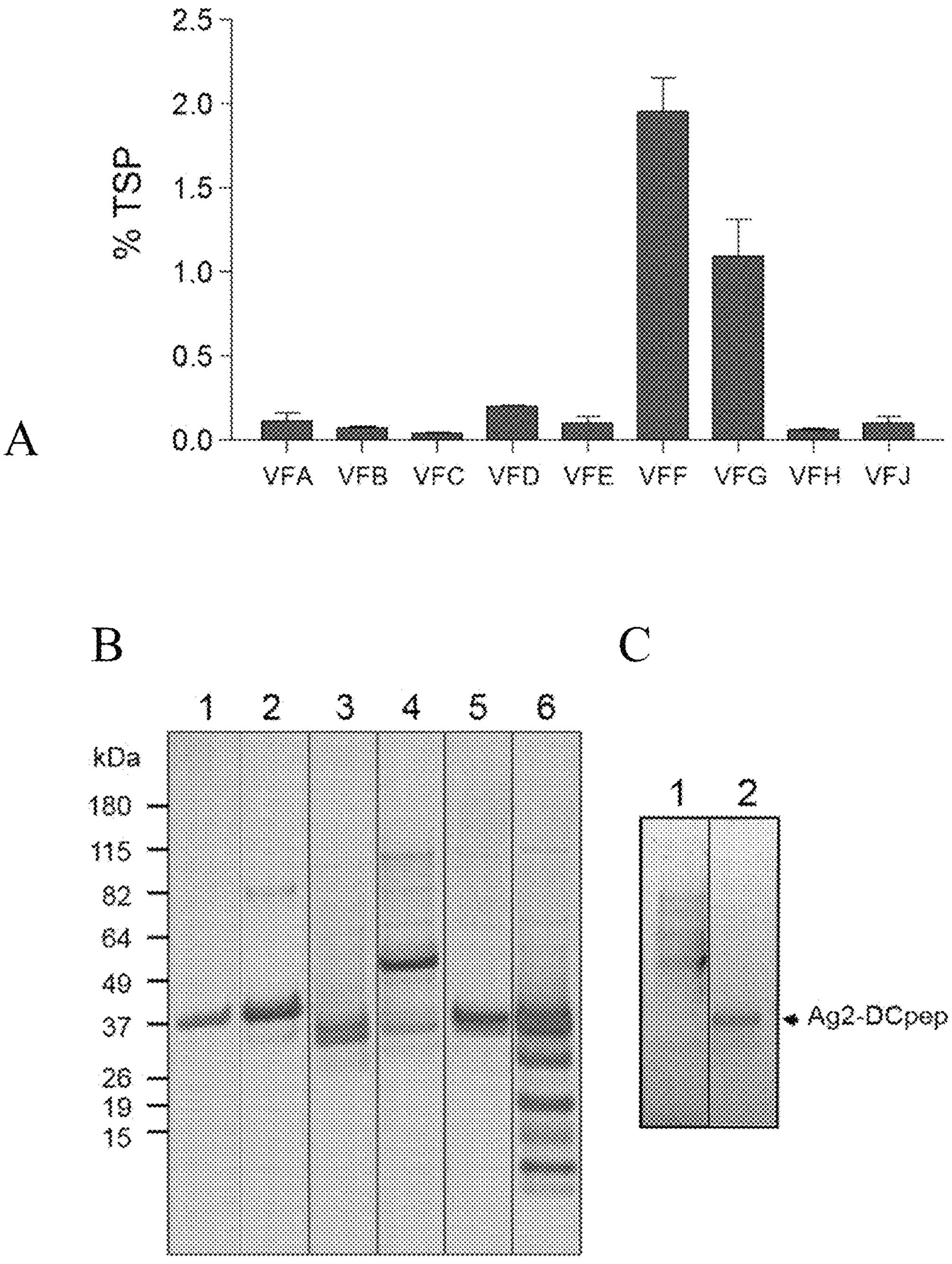
FIG. 8 are a graph and gels with (A) showing quantification of Ag2 production in maize. Accumulation of Ag2 proteins in top 10% of T1 seeds from each of the nine Ag2-gene-construct transformed maize lines was measured and presented as percent TSP (mean±standard error). B and C are Wester blots showing analysis of maize-derived recombinant Ag2 proteins. Proteins were separated by gel electrophoresis, transferred to nitrocellulose membrane and probed with an anti-Ag2 antibody. (A) Protein samples were from the *E. coli* expressed recombinant Ag2 (1 μg, lane 1; 5 μg, lane 2) or crude seed extracts from VFE (lane 3), VFF (lane 4), VFG (lane 5) and VFH (lane 6) transformed corn lines. (B) Proteins were isolated from un-transformed (lane 1) or VFG (lane 2) transformed corn seeds by anti-Ag2 affinity chromatography. The detection of Ag2-DCpep (~35 kDa) isolated from VFG seeds was indicated with an arrow.
Figure 9:
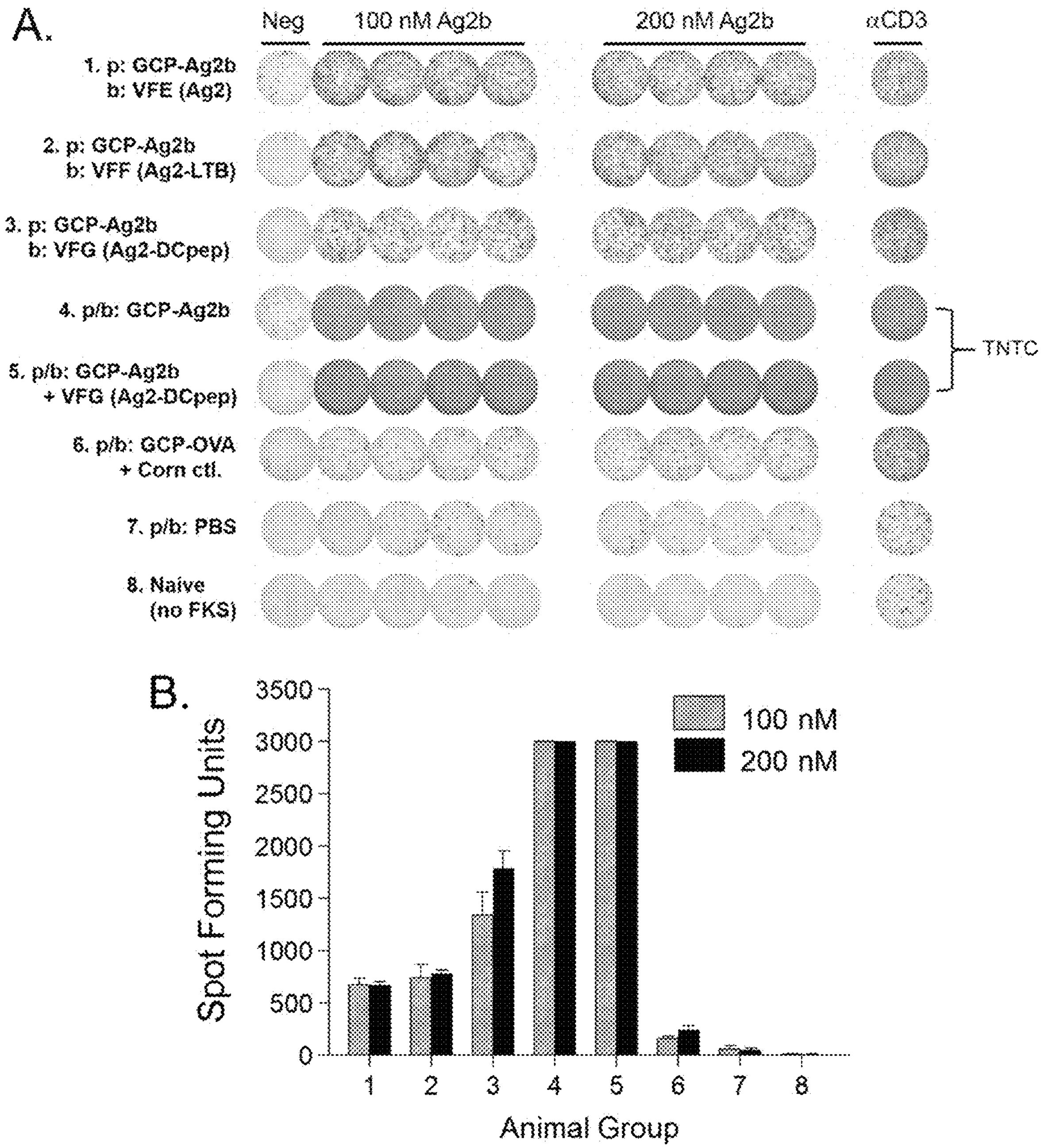
FIG. 9 are images of spot forming units (A) and a graph (B) showing results of vaccination with Ag2 induced cell-mediated Th17 immune response. Groups of mice were received one priming (p) and 3 boosting (b) doses of vaccine formulations as indicated in panel A. Immunogenic vaccines include bacterium-expressed recombinant Ag2 encapsulated with glucan-chitin-particles (GCP-Ag2b) and 3 types of maize-derived Ag2 in the form of edible wafers (VFE, VFF and VFG). GCP-OVA, wafer contained no Ag2 (corn ctl.) and PBS alone were used for mock vaccination. Vaccines were administrated by oral delivery for wafers and subcutaneous injection for GCP formulations. Vaccinated mice (groups 1-7) were challenged with formalin-killed-spherule (FKS) of *Coccidioides posadasii* and spleen removed for IL-17A ELISPOT analysis in a 96-well plate. Splenocytes were stimulated with Ag2b (100 and 200 nM), anti-CD3 antibody (αCD3) or untreated (Neg). Splenic cells that secreted IL-17A were visualized in (A) and quantified as spot forming units (B) with a maximal count of 3,000 per well. TNTC, too numerous to count.

The relative levels of Ag2 were estimated using an ELISA with the bacteria-produced Ag2 as the standard. Over 1500 seeds representing the various transformation events were analyzed individually and the mean of the top 10% of highest expressing seeds were used to rank the potential for each construct to overproduce the antigen[11]. The highest levels of Ag2 were from VFF (Ag2 fused to LT-B) with a mean of 1.95% of total soluble protein (TSP), or 475 mg/kg, and the highest recorded seed producing 3.99% TSP (1388 mg/kg) (FIG. 8). The next highest mean was from VFG (Ag2 fused to DCpep) with a mean Ag2 concentration of 1.09% TSP, or 256 mg/kg, and the highest single seed accumulating 3.07% TSP (711 mg/kg). Subcellular localization affected accumulation of Ag2, as demonstrated when comparing constructs VFA (plant vacuolar signal), VFB (plant cell wall signal) and VFC (plant ER signal). A construct with the native signal fungal Ag2 targeting signal was also compared to the plant signal sequence. The top 10% of expressing VFA and VFJ seed demonstrated the highest mean Ag2 accumulations of 0.11% and 0.10% TSP, respectively, VFB a mean Ag2 of 0.07% TSP and VFC seed the lowest mean of 0.04% TSP. Using an enhanced promoter in construct VFD, higher levels of Ag2 (0.20% TSP) could be obtained compared to VFB with the same subcellular location. Two transcription units in tandem (VFE) express somewhat more (0.10% TSP) than the equivalent single transcription unit (VFB). Driving Ag2 expression with an endosperm promoter (VFH) compared to an embryo promoter (VFB) resulted in approximately the same accumulation of recombinant antigen based on whole seed. VFF and VFG were clearly superior in over accumulation of Ag2 compared to all other constructs.

Western blot analysis was further used to determine protein integrity and the size of the recombinant Ag2 produced in maize. The results of representative seed extracts from selected constructs show all of the maize-derived Ag2 displayed a major band just slightly smaller in molecular weight to the *E. coli*-derived Ag2 with the exception of VFF that contains the LT-B fusion protein, which accounts for the much larger size.

Formulation of Ag2-Based Vaccines

Two types of Ag2 formulations were prepared for vaccine evaluation. One vaccine formulation is wafers made of Ag2-expressing corn seeds for oral delivery; the other is formulated for subcutaneous (s.c.) injection by encapsulation of soluble Ag2 with glucan-chitin-particles (GCP). To prepare maize wafers for oral delivery of the maize-derived Ag2, seed from VFE, VFF, and VFG representing Ag2, Ag2-LTB and Ag2-DCpep were bulked and ground to a flour-like consistency. These flours were then formed into wafer-like tablets and Table 1 shows the Ag2 concentration in wafers for each construct and that no antigen was lost during the production of the wafers. Control wafers were included in the analysis and no Ag2 was detected in either the parent material or the wafers.

TABLE 1

Ag2 concentrations in Wafers used for oral vaccine delivery

| | parent material (mg/kg) | wafers (mg/kg in flour) |
|---|---|---|
| VFE | 7 | 10 |
| VFF | 165 | 173 |
| VFG | 158 | 153 |
| Control | Below detection | Below detection |

For vaccine candidates used for subcutaneous injection, the soluble Ag2-DCpep was isolated from the VFG seed extracts by an anti-Ag2 affinity chromatography. FIG. 8B shows a Western blot of the seed extract and the eluate from the antibody column. Because of the limited amount of seed available at the time, there was not enough protein to be detected on a Coomassie stained gel. The purified maize Ag2-DCpep (~0.1 μg) was mixed with 25 μg mouse serum album and then encapsulated into GCPs (200 μg) to make the GCP-Ag2m vaccine (per dose). Similarly, we generated a GCP-Ag2b vaccine using bacterial expressed Ag2 (1 μg per dose) and a control GCP-OVA (1 μg ovalbumin per dose) without Ag2.

Vaccination of Mice with Maize-Derived Ag2 Induced a Cell-Mediated Immune Responses To assess Ag2 vaccination induced immune responses, we vaccinated 7 groups of mice with various vaccine formulations/regimens and challenged the mice with formalin-killed spherules (FKS) of *Coccidioides*. Spleen was collected to make splenocyte suspension for T-cell recall assay by IL-17A ELISPOT and lungs were used for immune T-cell recruitment/activation assessment by flow cytometry. All 7 groups of mice were received a prime vaccination followed by 3 booster doses 2 weeks apart. The first 4 groups of mice were primed with GCP-Ag2b by subcutaneous injection, and then boosted with orally delivered VFE (Ag2, group 1), VFF (Ag2-LTB, group 2), or VFG (Ag2-DCpep, group 3) wafers or s.c. injection of GCP-Ag2b (group 4). Mice in groups 5-7 received the same vaccinated materials for their priming and boosting doses, which consist of a combination of GCP-Ag2b (s.c.) and VFG wafers (oral) (group 5), a combination of GCP-OVA (s.c.) and control wafers without no Ag2 (oral) (group 6), and PBS (s.c. group 7). Mice fed on the wafers ad libitum and were estimated to ingest 0.1 mg of VFE Ag2, 1.5 mg of VFF, and 1.5 mg of VFG per dose, based on consumption estimates and wafer Ag2 concentrations.

Figure 11:
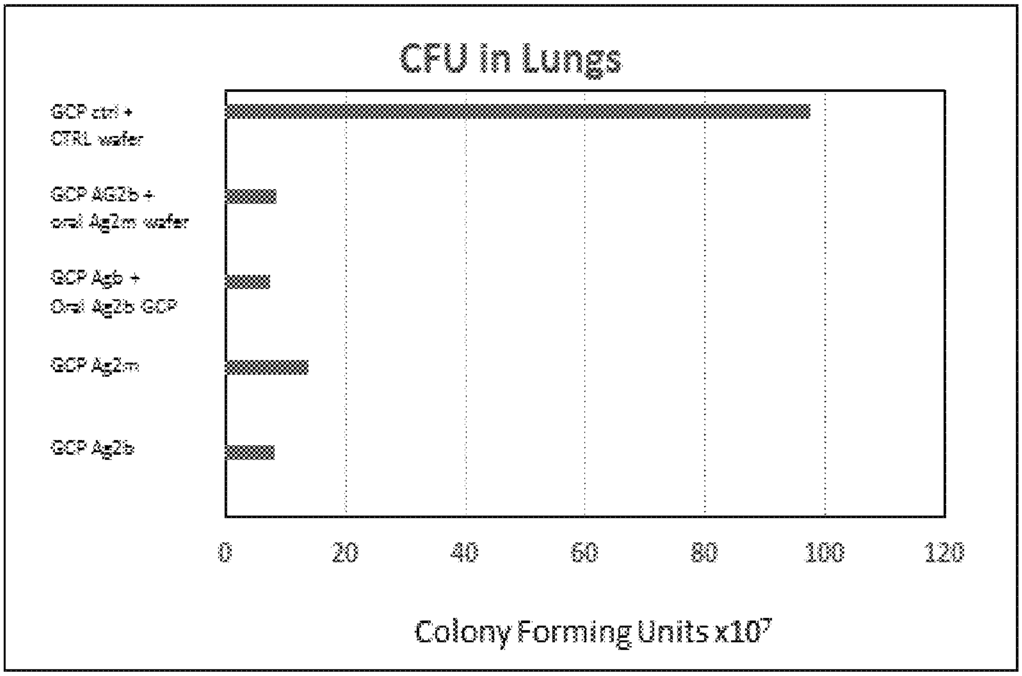
FIG. 11 is a graph showing results of immunization with bacterium- and maize-expressed Ag2 protected pulmonary coccidioidomycosis. Mice (n=10 per group) were vaccinated with GCP-Ag2b, GCP-Ag2m or GCP alone and challenged intranasally with a lethal dose of *C. posadasii*. Lung fungal burden was measured at 14 days after challenge. *p<0.05, **p<0.005 by Mann-Whitney U test.

Mice in all treatments were FKS-challenged 3 weeks after the last dose and assessed for immune response one week after the challenge. Naïve mice (group 8) without vaccination nor FKS challenge also were used as a control for immunoassays. Splenocytes from each group of mice were stimulated with Ag2b (100 and 200 nM; antigen-specific) and anti-CD3 (mitogenic positive control), or untreated (medium, negative control). Numbers of IL-17A secreting cells were quantified by ELISPOT assay. As shown in FIG. 11, minimal numbers of IL-17A secreting splenocytes were presented in all untreated samples; however, the numbers increased significantly in all groups upon anti-CD3 antibody treatment suggesting the obtained splenocytes were receptive to antigen stimulation. It is evident that vaccination with 4 doses of GCP-Ag2b induced robust and highest Th17 cellular immune response (FIG. 11, groups 4 and 5). The conditions for the assay were at saturation for groups 4 and 5, therefore the extent of additive effect of oral VFG vaccination on inducing Th17 immunity requires confirmation. Mice received booster doses by ingestion of the Ag2 fused to DCpep (Group 3, VFG material) showed an increased response over, Ag2 alone or Ag2 fused to LTB (VFE and VFF, groups 1 and 2, respectively).

Priming and boosting with GCP-Ag2b (group 4) enhanced the recruitment of IFN-γ-(Th1) and IL-17A-producing T cells (FIG. 10). There was a slight increase in the response when combined with VFG oral vaccine (group 5) but this was not statistically significant. The assay was at or near maximal for both groups, therefore it was not possible to resolve the effect conclusively.

Serum was analyzed for IgG and a progressive increase in IgG was observed in mice for groups 1-5 with titers of $10^3$ for groups 1-3 and $10^4$ for groups 4 and 5 (data not shown). A significant increase in serum IgA was only detected in group 4 and 5 mice.

Vaccination with Purified Maize-Expressed Recombinant Ag2m Reduced Fungal Burden Following Pulmonary *C. posadasii* Challenge Ingestion of rAg2-DCpep expressing VFG wafer seems to slightly enhanced Th1 and Th17 response (FIG. 11, group 3 and FIG. 12 group 5), that are critical for control of pulmonary *Coccidioides* infection. To further assess the protective efficacy of rAg2-DCpep, we purified the antigen from VFG corn seeds by anti-Ag2 affinity chromatography and formulated a GCP-Ag2m vaccine. Groups of mice (n=10) were vaccinated twice with GCP-Ag2m, GCP-Ag2b or GCP without Ag2 by s.c. injection and challenged intranasally with a lethal dose of *C. posadasii* 2 weeks after the booster. Fungal burden in the lungs were assessed at day 14 post challenge. As shown in FIG. 11, compared to GCP-alone vaccination, GCP-Ag2b and GCP-Ag2m were able to significantly reduce the fungal burden in the lungs by an average of 92% and 82%, respectively. It is noted that GCP-Ag2m contains only approximately 0.1 μg of Ag2-DCpep, while GCP-Ag2b consist of 1 μg Ag2 per vaccine dose. T here was no significant difference in the reduction of fungal burden between maize and bacteria-produced Ag2.

Figure 12:
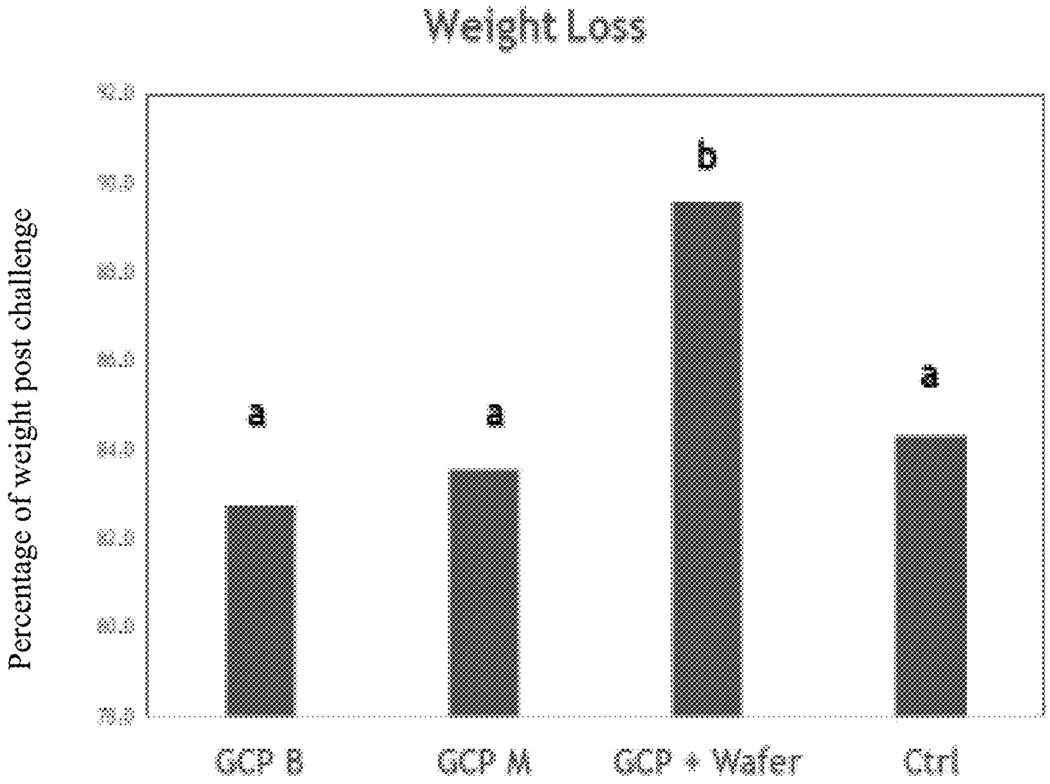
FIG. 12 is a chart showing weight post challenge.

The body weight of mice were monitored prior to and after fungal challenge. When mice were administered the paired dosing (oral and s.c.), this was the only treatment that reduced the loss of body weight (FIG. 12). This confirms earlier results from above that the paired dosing can improve the efficacy of the vaccination.

Discussion

The GPI-anchored antigen, Ag2, is a likely candidate for a subunit vaccine for Valley Fever, but its poor accumulation in microbial hosts hinders commercialization. Therefore, maize, which has been used for other problematic recombinant proteins was attempted as an alternative host. For many recombinant proteins including the hepatitis B surface antigen (HBsAg), the protein is most highly accumulated when using an embryo preferred cell wall targeting signal[22,30]. In some cases, such as the LTB antigen, it is most highly accumulated when using a vacuolar targeting signal. Fusion to LTB can also increase accumulation of recombinant proteins[20] (and unpublished results). The ER has shown to be the preferred location for yet other recombinant proteins such as cellulases[33]. While the most success has come when targeted to the embryo, butyrylcholinesterase is a case where the highest accumulation occurred when using an endosperm-preferred promoter and an ER-targeting signal[34].

This led to the evaluation of constructs targeting these different tissues and intracellular locations. For the Ag2 recombinant protein, we established that the vacuolar targeting sequence produces the highest levels of accumulation. We also observed that a fusion protein at the C-terminal end of Ag2 can increase accumulation by more than 10-fold, presumably due to stabilization of the protein. This effect does not require a large string of amino acid sequences as the DCpep is only 12 amino acids long, but accumulation was greatly enhanced by the longer sequence in the LTB-fused Ag2 construct. Some of this stabilization may be related to whether the C-terminal GPI anchoring signal is cleaved from the Ag2 protein.

Analysis on Western gels of the maize-produced Ag2 showed that most constructs had a cross reacting band slightly smaller than that of Ag2 produced in bacteria. As can be seen in the Western blot (FIG. 3A), construct VFE displays a doublet, with the presumed uncleaved protein retaining the GPI anchor as the top band, and the GPI anchor-cleaved protein as the smaller band. This hypothesis is supported by the fact that the VFG lines (Ag2:DCpep) show a more intense top band, and GPI anchor prediction programs fail to predict cleavage once the peptide is added to the C terminus of Ag2. Interestingly, although accumulation levels of Ag2 in the embryo and endosperm seem to be approximately equivalent by ELISA, the endosperm-targeted Ag2 seems to undergo degradation or proteolysis, as shown in FIG. 3. A much more detailed physical analysis of the recombinant protein is planned to clarify the differences in protein structure.

Some VFF first generation single seed demonstrated levels greater than 1,000 mg/kg for the recombinant antigen. Optimization of recombinant proteins in maize have shown a minimum of a 10-fold increase and there are examples of proteins yielding 2 g/kg in whole seed[11]. The recombinant protein concentration can be further increased another 7-fold by fractionation of the seed by retaining the embryo fraction. These levels of improvement by breeding and fractionation have been obtained for other recombinant proteins, such as HBsAg[22] and LTB[35]. These accumulation levels hold great promise for a low cost subunit vaccine as they should be greater than 100-fold higher than when produced in *E. coli*. Grain from one of the constructs, VFG, was used to purify the antigen using an antibody affinity column. This approach appeared to be a useful method for analytical purposes. However, for large-scale production, a more conventional purification will need to be established using ionic exchange columns and size chromatography. The much higher concentrations, seen in maize grain should make this possible and will be pursued in the future.

All indications to date suggest that maize could be a useful host to accumulate the Ag2 but a much more in depth physical characterization is needed. Prior to undertaking this detailed study, we wished to investigate a key assumption; specifically, is the immune response elicited with maize-produced material comparable to that of Ag2 made in microbes. When the purified maize-produced Ag2 was compared with the bacterial produced Ag2, both showed a reduction in the fungal burden after challenge when administered in GCPs subcutaneously. A more detailed study is required to understand whether there are quantitative differences however the maize-derived material appears to be an effective immunogen.

Having an ample supply of antigen is a key requirement for subunit vaccines but it is also critical to understand the best way to administer the vaccine to provide a protective response. Previous work has shown that for this pathogen, a strong mucosal response is required. Most traditional vaccines are parenterally administered which provides little or no mucosal immune response. Previous reports have demonstrated that GCP particles can induce strong Th1 and Th17 responses, indicative of protection[19] using a *Coccidioides* antigen. This was confirmed in this study and both maize and *E. coli* derived Ag2 were able to reduce the fungal load in the lungs.

Reports using orally-delivered maize grain have also shown success in eliciting a strong mucosal response for other antigens. Therefore, a combination of oral and GCP injected vaccine candidates were tested to determine whether a strong protective immune response could be obtained[36,37]. The FKS challenge showed that the oral wafers using the DCpep provided a better Th17 response in splenocytes than the other wafers tested. This is not likely due to concentration alone as the VFF material had the same concentration of Ag2 therefore the DCpep may enhance the immune response.

The combination of GCPs and oral wafers may have had an improvement over injected doses alone however, due to the fact that immune response detection methods used were saturated in the FKS challenge study, it was not possible to determine whether this was significant. However, the reduction of the loss of body weight when challenged confirms that this is a more efficacious approach. With the future abundance of Ag2-grain, more detailed studies will be undertaken to evaluate the effect of higher concentrations of orally administered wafers and maize-derived Ag2 loaded into GCPs.

Conclusion

High levels of Ag2 in maize grain have been developed which promise to produce Ag2 at concentrations of grams of Ag2/kg grain. These lines have the potential for economically feasible production of the protein for a commercial vaccine. Promising data have been generated in the mouse model to indicate that the maize-produced Ag2 protein can provide protection from the pathogen. Additional studies are required to; a) optimize Ag2 accumulation in maize, b) develop an efficient purification process, c) characterize the Ag2 from maize and d) develop the optimal vaccination regime.

References for Example 5

[1] Tarcha, E. J., Basrur, V., Hung, C.-Y., Gardner, M. J., and Cole, G. T. (2006) Multivalent recombinant protein vaccine against coccidioidomycosis, *Infect Immun* 74, 5802-5813.

[2] Smith, C. E., and Beard, R. R. (1946) Varieties of coccidioidal infection in relation to the epidemiology and control of the diseases, *American Journal of Public Health and the Nations Health* 36, 1394-1402.

[3] Nguyen, C., Barker, B. M., Hoover, S., Nix, D. E., Ampel, N. M., Frelinger, J. A., Orbach, M. J., and Galgiani, J. N. (2013) Recent advances in our understanding of the environmental, epidemiological, immunological, and clinical dimensions of coccidioidomycosis, *Clinical Microbiology Reviews* 26, 505-525.

[4] Pappagianis, D. (2001) Seeking a Vaccine against *Coccidioides immitis* and Serologic Studies: Expectations and Realities, *Fungal Genetics and Biology* 32, 1-9.

[5] Borchers, A. T., and Gershwin, M. E. (2010) The immune response in *Coccidioidomycosis, Autoimmunity Reviews* 10, 94-102.

[6] Fisher, B. T., Chiller, T. M., Prasad, P. A., Beveridge, M., Walsh, T. J., and Zaoutis, T. E. (2010) Hospitalizations for coccidioidomycosis at forty-one children's hospitals in the United States, *The Pediatric Infectious Disease Journal* 29, 243-247.

[7] CDC. (2013) Increase in reported coccidioidomycosis—United States, 1998-2011, *Morbidity and Mortality Weekly Report* 62, 217-221.

[8] Cole, G. T., Hung, C.-Y., Sanderson, S. D., Hurtgen, B. J., Wiithrich, M., Klein, B. S., Deepe, G. S., Ostroff, G. R., and Levitz, S. M. (2013) Novel strategies to enhance vaccine immunity against coccidioidomycosis, *PLoS pathogens* 9, e1003768.

[9] Herr, R. A., Hung, C.-Y., and Cole, G. T. (2007) Evaluation of two homologous proline-rich proteins of *Coccidioides posadasii* as candidate vaccines against coccidioidomycosis, *Infect Immun* 75, 5777-5787.

[10] Shubitz, L. F., Yu, J.-J., Hung, C.-Y., Kirkland, T. N., Peng, T., Perrill, R., Simons, J., Xue, J., Herr, R. A., and Cole, G. T. (2006) Improved protection of mice against lethal respiratory infection with *Coccidioides posadasii* using two recombinant antigens expressed as a single protein, *Vaccine* 24, 5904-5911.

[11] Hood, E. E., Devaiah, S. P., Fake, G., Egelkrout, E., Teoh, K. T., Requesens, D. V., Hayden, C., Hood, K. R., Pappu, K. M., and Carroll, J. (2012) Manipulating corn germplasm to increase recombinant protein accumulation, *Plant biotechnology journal* 10, 20-30.

[12] Masarik, M., Kizek, R., Kramer, K. J., Billova, S., Brazdova, M., Vacek, J., Bailey, M., Jelen, F., and Howard, J. A. (2003) Application of avidin-biotin technology and adsorptive transfer stripping square-wave voltammetry for detection of DNA hybridization and avidin in transgenic avidin maize, *Anal Chem* 75, 2663-2669.

[13] Howard, J. A., and Hood, E. E. (2016) *Commercial Plant-produced Recombinant Protein Products*, Springer.

[14] Paul, M., and Ma, J. K. (2010) Plant-made immunogens and effective delivery strategies, *Expert Reviews* 9, 821-833.

[15] Tacket, C. O., Pasetti, M. F., Edelman, R., Howard, J. A., and Streatfield, S. (2004) Immunogenicity of recombinant LT-B delivered orally to humans in transgenic corn, *Vaccine* 22, 4385-4389.

[16] Mohamadzadeh, M., Duong, T., Sandwick, S. J., Hoover, T., and Klaenhammer, T. R. (2009) Dendritic cell targeting of Bacillus anthracis protective antigen expressed by *Lactobacillus acidophilus* protects mice from lethal challenge, *Proc Natl Acad Sci USA* 106, 4331-4336.

[17] Mirza, Z., Soto, E. R., Dikengil, F., Levitz, S. M., and Ostroff, G. R. (2017) Beta-Glucan Particles as Vaccine Adjuvant Carriers, *Vaccines for Invasive Fungal Infections: Methods and Protocols,* 143-157.

[18] Huang, H., Ostroff, G. R., Lee, C. K., Specht, C. A., and Levitz, S. M. (2013) Characterization and optimization of the glucan particle-based vaccine platform, *Clinical and Vaccine Immunology* 20, 1585-1591.

[19] Hung, C.-Y., Zhang, H., Castro-Lopez, N., Ostroff, G. R., Khoshlenar, P., Abraham, A., Cole, G. T., Negron, A., Forsthuber, T., and Peng, T. (2018) Glucan-chitin particles enhance Th17 response and improve protective efficacy of a multivalent antigen (rCpal) against pulmonary *Coccidioides posadasii* infection, *Infect Immun*, IAI. 00070-00018.

[20] Streatfield, S., Jilka, J., Hood, E., Turner, D., Bailey, M., Mayor, J., Woodard, S., Beifuss, K., Horn, M., and Delaney, D. (2001) Plant-based vaccines: unique advantages, *Vaccine* 19, 2742-2748.

[21] Holwerda, B. C., Padgett, H. S., and Rogers, J. C. (1992) Proaleurain vacuolar targeting is mediated by short contiguous peptide interactions, *The Plant Cell* 4, 307-318.

[22] Hayden, C. A., Egelkrout, E. M., Moscoso, A. M., Enrique, C., Keener, T. K., Jimenez-Flores, R., Wong, J. C., and Howard, J. A. (2012) Production of highly concentrated, heat-stable hepatitis B surface antigen in maize, *Plant biotechnology journal* 10, 979-984.

[23] Russell, D. A., and Fromm, M. E. (1997) Tissue-specific expression in transgenic maize of four endosperm promoters from maize and rice, *Transgenic research* 6, 157-168.

[24] An, G., Mitra, A., Choi, H. K., Costa, M. A., An, K., Thornburg, R. W., and Ryan, C. A. (1989) Functional analysis of the 3'control region of the potato wound-inducible proteinase inhibitor II gene, *The Plant Cell I,* 115-122.

[25] Streatfield, S. J., Mayor, J. M., Barker, D. K., Brooks, C., Lamphear, B. J., Woodard, S. L., Beifuss, K. K., Vicuna, D. V., Massey, L. A., and Horn, M. E. (2002) Development of an edible subunit vaccine in corn against enterotoxigenic strains of *Escherichia coli, In Vitro Cellular & Developmental Biology-Plant* 38, 11-17.

[26] Hood, E. E., Bailey, M. R., Beifuss, K., Magallanes-Lundback, M., Horn, M. E., Callaway, E., Drees, C., Delaney, D. E., Clough, R., and Howard, J. A. (2003) Criteria for high-level expression of a fungal laccase gene in transgenic maize, *Plant Biotechnology Journal* 1, 129-140.

[27] Streatfield, S. J., Jilka, J. M., Hood, E. E., Turner, D. D., Bailey, M. R., Mayor, J. M., Woodard, S. L., Beifuss, K. K., Horn, M. E., Delaney, D. E., and Howard, J. A. (2001) Plant-based vaccines: unique advantages, *Vaccine* 19, 2742-2748.

[28] Hayden, C., Smith, E., Turner, D. D., Keener, T. K., Wong, J. C., Walker, J. H., Tizard, I. R., Jimenez-Flores, R., and Howard, J. A. (2014) Supercritical Fluid Extraction Provides an Enhancement to the Immune Response for Orally-Delivered Hepatitis B Surface Antigen, *Vaccine in press.*

[29] Hurtgen, B. J., Hung, C.-Y., Ostroff, G. R., Levitz, S. M., and Cole, G. T. (2012) Construction and evaluation of a novel recombinant T cell epitope-based vaccine against coccidioidomycosis, *Infect Immun* 80, 3960-3974.

[30] Hayden, C. A., Streatfield, S. J., Lamphear, B. J., Fake, G. M., Keener, T. K., Walker, J. H., Clements, J. D., Turner, D. D., Tizard, I. R., and Howard, J. A. (2012) Bioencapsulation of the hepatitis B surface antigen and its use as an effective oral immunogen, *Vaccine* 30, 2937-2942.

[31] Hung, C.-Y., Gonzalez, A., Wiithrich, M., Klein, B. S., and Cole, G. T. (2011) Vaccine immunity to coccidioidomycosis occurs by early activation of three signal pathways of T helper cell response (Th1, Th2, and Th17), *Infection and Immunity* 79, 4511-4522.

[32] Delgado, N., Xue, J., Yu, J.-J., Hung, C.-Y., and Cole, G. T. (2003) A recombinant β-1, 3-glucanosyltransferase homolog of *Coccidioides posadasii* protects mice against coccidioidomycosis, *Infection and Immunity* 71, 3010-3019.

[33] Hood, E., Love, R., Lane, J., Bray, J., Clough, R., Pappu, K., Drees, C., Hood, K., Yoon, S., and Ahmad, A. (2007) Subcellular targeting is a key condition for high-level accumulation of cellulase protein in transgenic maize seed, *Plant biotechnology journal* 5, 709-719.

[34] Egelkrout, E., Hayden, C., Wales, M., Walker, J., Novikov, B., Grimsley, J., and Howard, J. (2017) Production of the bioscavenger butyrylcholinesterase in maize, *Molecular Breeding* 37,136.

[35] Lamphear, B., Streatfield, S., Jilka, J., Brooks, C., Barker, D., Turner, D., Delaney, D., Garcia, M., Wiggins, B., and Woodard, S. (2002) Delivery of subunit vaccines in maize seed, *Journal of Controlled Release* 85, 169-180.

[36] Wu, H., Singh, N. K., Locy, R. D., Scissum-Gunn, K., and Giambrone, J. J. (2004) Immunization of chickens with VP2 protein of infectious bursal disease virus expressed in *Arabidopsis thaliana, Avian Diseases* 48, 663-668.

[37] Lappalainen, S., Pastor, A. R., Malm, M., Lopez-Guerrero, V., Esquivel-Guadarrama, F., Palomares, L. A., Vesikari, T., and Blazevic, V. (2015) Protection against live rotavirus challenge in mice induced by parenteral and mucosal delivery of VP6 subunit rotavirus vaccine, *Archives of Virology,* 1-4.

What is claimed is:

1. A method of increasing a protective response to a hepatitis B or *Coccidioides* vaccine, the method comprising, administering to an animal, at least one paired administration of a vaccine comprising a nucleic acid molecule and/or polypeptide of hepatitis B or *Coccidioides*, said administration comprising an oral administration of said vaccine and a non-oral administration of said vaccine, wherein said oral administration is an oral administration of a composition comprising a plant or plant part comprising said nucleic acid molecule and/or polypeptide, wherein said oral and non-oral vaccines are administered within three days from the other said administration of said vaccines producing an increased protective response compared to an animal not administered said vaccine.

2. The method of claim 1, comprising, i) a first paired administration of said vaccine comprising an oral administration of said vaccine and a non-oral administration of said vaccine, wherein said oral and non-oral vaccines are administered within three days from the other; and ii) a second paired administration of said vaccine comprising an oral administration of said vaccine and a non-oral administration of said vaccine, wherein said oral and non-oral vaccines are administered within three days from each other.

3. The method of claim 1, wherein said animal has increased protective response compared to an animal administered three parental administrations of said vaccine, each said parental administered within two weeks or more of the other.

4. The method of claim 2, wherein said second paired administration is administered one to four weeks after administration of said first paired administration.

5. The method of claim 1, wherein said vaccine produces a serum and mucosal immune response.

6. The method of claim 3, wherein said administration produces IgA and/or IgG antibodies in said animal higher than said three non-oral administrations.

7. The method of claim 1, wherein said administration produces increased numbers of T-cells.

8. The method of claim 1, wherein said vaccine comprises a nucleic acid molecule of hepatitis B or *Coccidioides.*

9. The method of claim 8, wherein said nucleic acid molecule is introduced into a plant and said plant expresses a nucleic acid molecule.

10. The method of claim 1, wherein said oral administration is an oral administration of a composition comprising said plant or plant part comprising said nucleic acid molecule.

11. The method of claim 10, wherein said plant or plant part comprises maize.

12. The method of claim 1, wherein said vaccine comprises hepatitis B surface antigen or *Coccidioides* antigen 2.

13. The method of claim 10, said vaccine further comprising sugar.

14. The method of claim 1, said vaccine further comprising a microcrystalline delta inulin polysaccharide-based adjuvant.

15. The method of claim 1, wherein said animal has increased weight following administration of said vaccine.

16. The method of claim 1, comprising administering to an animal, i) a first paired administration of said vaccine comprising an oral administration of a plant or plant part comprising said nucleic acid molecule and/or said polypeptide, and a non-oral administration of a vaccine comprising said nucleic acid molecule and/or polypeptide, wherein said oral and non-oral vaccines are administered within three days from the other; and ii) a second paired administration of said vaccine comprising an oral administration of a plant or plant part comprising said nucleic acid molecule and/or said polypeptide, and a non-oral administration of a vaccine comprising said nucleic acid molecule and/or polypeptide, wherein said oral and non-oral vaccines are administered within three days from the other, said second paired administration administered at least two weeks after administration of said first paired administration; and iii) producing in said animal an increased serum and mucosal response compared to administering a primer and two boosting parental administrations of said vaccine.

17. A method of reducing the number of booster vaccinations and protecting an animal from hepatitis B or *Coccidioides*, the method comprising, administering to an animal, i) a priming paired administration of a vaccine comprising a nucleic acid molecule and/or polypeptide of hepatitis B or *Coccidioides*, said administration comprising an oral administration of said vaccine and a non-oral administration of said vaccine, wherein said oral and non-oral vaccines are administered within three days from the other; and ii) a booster paired administration of said vaccine comprising an oral administration of said vaccine and a non-oral administration of said vaccine, wherein said oral and non-oral vaccines are administered within three days from each other, wherein said oral administration is an oral administration of a composition comprising a plant or plant part comprising said nucleic acid molecule and/or polypeptide, said method producing the same or an increased protective response compared to administering a primer and two boosting parental administrations of said vaccine.

18. The method of claim 17, comprising producing in said animal serum and mucosal antibodies.

19. The method of claim 17, comprising producing in said animal increased IgG and/or IgA antibodies.

* * * * *